(12) United States Patent
Mathies et al.

(10) Patent No.: US 8,454,906 B2
(45) Date of Patent: Jun. 4, 2013

(54) MICROFABRICATED DROPLET GENERATOR FOR SINGLE MOLECULE/CELL GENETIC ANALYSIS IN ENGINEERED MONODISPERSED EMULSIONS

(75) Inventors: Richard A. Mathies, San Francisco, CA (US); Palani Kumaresan, Los Angeles, CA (US); Chaoyang Yang, Xiamen (CN); Robert G. Blazej, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 425 days.

(21) Appl. No.: 12/670,377

(22) PCT Filed: Jul. 24, 2008

(86) PCT No.: PCT/US2008/071086
§ 371 (c)(1),
(2), (4) Date: May 11, 2010

(87) PCT Pub. No.: WO2009/015296
PCT Pub. Date: Jan. 29, 2009

(65) Prior Publication Data
US 2010/0285975 A1    Nov. 11, 2010

Related U.S. Application Data

(60) Provisional application No. 60/962,059, filed on Jul. 25, 2007, provisional application No. 60/961,926, filed on Jul. 24, 2007.

(51) Int. Cl.
*B01L 3/00*    (2006.01)
*B01L 3/02*    (2006.01)
*G01N 1/10*    (2006.01)

(52) U.S. Cl.
USPC ........... 422/505; 422/501; 422/502; 422/503; 422/504; 422/515; 422/521; 422/417; 436/180

(58) Field of Classification Search
USPC ................. 422/502–505, 417, 501, 515, 521; 435/287.1; 436/180
See application file for complete search history.

(56) References Cited

U.S. PATENT DOCUMENTS 3,190,310 A    6/1965    Honsinger
3,636,334 A    1/1972    Svoboda
(Continued)

FOREIGN PATENT DOCUMENTS

CA    2433145 A1    5/2002
CN    101449089    6/2009
(Continued)

OTHER PUBLICATIONS

U.S. Appl. No. 12/026,510, filed Feb. 5, 2008, Jovanovich et al.
(Continued)

*Primary Examiner* — Brian R Gordon
(74) *Attorney, Agent, or Firm* — Weaver Austin Villeneuve & Sampson LLP

(57) ABSTRACT

Provided are microfluidic designs and methods for rapid generation of monodisperse nanoliter volume droplets of reagent/target (e.g., molecule or cell) mix in emulsion oil. The designs and methods enable high-throughput encapsulation of a single target (e.g., DNA/RNA molecules or cells) in controlled size droplets of reagent mix. According to various embodiments, a microfabricated, 3-valve pump is used to precisely meter the volume of reagent/target mix in each droplet and also to effectively route microparticles such as beads and cells into the device, which are encapsulated within droplets at the intersection of the reagent channel and an oil channel. The pulsatile flow profile of the microfabricated pumps provides active control over droplet generation, thereby enabling droplet formation with oils that are compatible with biological reactions but are otherwise difficult to form emulsions with.

19 Claims, 11 Drawing Sheets

U.S. PATENT DOCUMENTS

| | | |
|---|---|---|
| 3,768,521 A | 10/1973 | Brychta et al. |
| 4,304,257 A | 12/1981 | Webster |
| 4,357,675 A | 11/1982 | Freyman |
| 4,558,845 A | 12/1985 | Hunkapiller |
| 4,703,913 A | 11/1987 | Hunkapiller |
| 4,963,498 A | 10/1990 | Hillman et al. |
| 5,157,284 A | 10/1992 | O'Connell et al. |
| 5,609,919 A * | 3/1997 | Yuan et al. ............ 427/426 |
| 5,635,358 A | 6/1997 | Wilding et al. |
| 5,639,428 A | 6/1997 | Cottingham |
| 5,726,026 A | 3/1998 | Wilding et al. |
| 5,842,787 A | 12/1998 | Kopf-sill et al. |
| 5,885,470 A | 3/1999 | Parce et al. |
| 5,942,443 A | 8/1999 | Parce et al. |
| 5,971,158 A | 10/1999 | Yager et al. |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,048,100 A | 4/2000 | Thrall et al. |
| 6,056,860 A | 5/2000 | Amigo et al. |
| 6,073,482 A | 6/2000 | Moles |
| 6,074,827 A | 6/2000 | Nelson et al. |
| 6,103,199 A | 8/2000 | Bjornson et al. |
| 6,120,184 A | 9/2000 | Laurence et al. |
| 6,136,212 A | 10/2000 | Mastrangelo et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,197,595 B1 | 3/2001 | Anderson et al. |
| 6,207,031 B1 | 3/2001 | Adourian et al. |
| 6,235,471 B1 | 5/2001 | Knapp et al. |
| 6,238,538 B1 | 5/2001 | Parce et al. |
| 6,251,343 B1 | 6/2001 | Dubrow et al. |
| 6,280,589 B1 | 8/2001 | Manz et al. |
| 6,319,476 B1 | 11/2001 | Victor, Jr. et al. |
| 6,321,791 B1 | 11/2001 | Chow |
| 6,322,683 B1 | 11/2001 | Wolk et al. |
| 6,348,318 B1 | 2/2002 | Valkirs |
| 6,379,929 B1 | 4/2002 | Burns et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,290 B1 | 8/2002 | Harrison et al. |
| 6,454,924 B2 | 9/2002 | Jedrzejewski et al. |
| 6,489,112 B1 | 12/2002 | Hadd et al. |
| 6,520,753 B1 | 2/2003 | Grosjean et al. |
| 6,521,188 B1 | 2/2003 | Webster |
| 6,524,456 B1 | 2/2003 | Ramsey et al. |
| 6,532,997 B1 | 3/2003 | Bedingham et al. |
| 6,533,914 B1 | 3/2003 | Liu |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,663,833 B1 | 12/2003 | Stave et al. |
| D486,156 S | 2/2004 | Lee et al. |
| 6,685,442 B2 | 2/2004 | Chinn et al. |
| 6,705,345 B1 | 3/2004 | Bifano |
| D488,818 S | 4/2004 | Lee et al. |
| 6,752,922 B2 | 6/2004 | Huang et al. |
| 6,764,648 B1 | 7/2004 | Roach et al. |
| 6,782,746 B1 | 8/2004 | Hasselbrink et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,824,663 B1 | 11/2004 | Boone |
| 6,829,753 B2 | 12/2004 | Lee et al. |
| 6,852,287 B2 | 2/2005 | Gancsan |
| 6,870,185 B2 | 3/2005 | Roach et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,097,809 B2 | 8/2006 | Van Dam et al. |
| 7,198,759 B2 | 4/2007 | Bryning et al. |
| 7,261,812 B1 * | 8/2007 | Karp et al. ............ 210/198.2 |
| 7,279,146 B2 | 10/2007 | Nassef et al. |
| 7,282,361 B2 | 10/2007 | Hodge |
| 7,312,611 B1 | 12/2007 | Harrison et al. |
| 7,323,305 B2 | 1/2008 | Leamon et al. |
| 7,438,856 B2 | 10/2008 | Jedrzejewski et al. |
| 7,445,926 B2 | 11/2008 | Mathies et al. |
| 7,488,603 B2 | 2/2009 | Gjerde et al. |
| 7,622,081 B2 * | 11/2009 | Chou et al. ............ 422/504 |
| 7,745,207 B2 | 6/2010 | Jovanovich et al. |
| 7,763,453 B2 | 7/2010 | Clemmens et al. |
| 7,766,033 B2 | 8/2010 | Mathies et al. |
| 7,799,553 B2 | 9/2010 | Mathies et al. |
| 7,867,763 B2 * | 1/2011 | Facer et al. ............ 435/303.1 |
| 8,105,553 B2 * | 1/2012 | Grossman et al. ............ 422/504 |
| 8,257,666 B2 * | 9/2012 | Quake et al. ............ 422/504 |
| 8,286,665 B2 | 10/2012 | Mathies et al. |
| 2001/0041357 A1 | 11/2001 | Fouillet et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0119480 A1 | 8/2002 | Weir et al. |
| 2002/0119482 A1 | 8/2002 | Nelson et al. |
| 2002/0127736 A1 | 9/2002 | Chou et al. |
| 2002/0139084 A1 | 10/2002 | Tobolka |
| 2002/0144738 A1 | 10/2002 | Unger et al. |
| 2002/0148992 A1 | 10/2002 | Hayenga et al. |
| 2002/0160361 A1 | 10/2002 | Loehrlein et al. |
| 2002/0187560 A1 | 12/2002 | Pezzuto et al. |
| 2003/0008308 A1 | 1/2003 | Enzelberger et al. |
| 2003/0021734 A1 | 1/2003 | Vann et al. |
| 2003/0070677 A1 | 4/2003 | Handique et al. |
| 2003/0217923 A1 | 11/2003 | Harrison et al. |
| 2004/0014091 A1 | 1/2004 | Duck et al. |
| 2004/0037739 A1 | 2/2004 | Mcneely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086872 A1 | 5/2004 | Childers et al. |
| 2004/0132170 A1 | 7/2004 | Storek et al. |
| 2004/0151629 A1 | 8/2004 | Pease et al. |
| 2004/0197845 A1 | 10/2004 | Hassibi et al. |
| 2004/0209354 A1 | 10/2004 | Mathies et al. |
| 2004/0224380 A1 | 11/2004 | Chou et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0155861 A1 | 7/2005 | Guzman |
| 2005/0161326 A1 | 7/2005 | Morita et al. |
| 2005/0161669 A1 | 7/2005 | Jovanovich et al. |
| 2005/0224134 A1 | 10/2005 | Yin et al. |
| 2005/0224352 A1 | 10/2005 | Harrison et al. |
| 2005/0241941 A1 | 11/2005 | Parce et al. |
| 2005/0255003 A1 | 11/2005 | Summersgill et al. |

| | | | | | | |
|---|---|---|---|---|---|---|
| 2005/0287572 | A1* | 12/2005 | Mathies et al. ............... 435/6 | JP | 2003/516129 A | 5/2003 |
| 2006/0027456 | A1 | 2/2006 | Harrison et al. | JP | 2006-512092 | 4/2006 |
| 2006/0057209 | A1 | 3/2006 | Chapman et al. | JP | 2008-500836 | 1/2008 |
| 2006/0073484 | A1 | 4/2006 | Mathies et al. | JP | 2009-530569 | 8/2009 |
| 2006/0076068 | A1 | 4/2006 | Young et al. | JP | 2011-234728 | 11/2011 |
| 2006/0140051 | A1 | 6/2006 | Kim et al. | WO | 93/22053 | 4/1993 |
| 2006/0163143 | A1 | 7/2006 | Chirica et al. | WO | 96/04547 A1 | 2/1996 |
| 2006/0186043 | A1 | 8/2006 | Covey et al. | WO | 98/10277 | 3/1998 |
| 2006/0266645 | A1 | 11/2006 | Chen et al. | WO | 98/52691 A1 | 11/1998 |
| 2007/0017812 | A1 | 1/2007 | Bousse | WO | 98/53300 A2 | 11/1998 |
| 2007/0034025 | A1 | 2/2007 | Pant et al. | WO | 98/53300 A3 | 11/1998 |
| 2007/0092914 | A1* | 4/2007 | Griffiths et al. ............. 435/7.1 | WO | 99/22868 | 5/1999 |
| 2007/0105163 | A1 | 5/2007 | Grate et al. | WO | 99/36766 A1 | 7/1999 |
| 2007/0122819 | A1 | 5/2007 | Wu et al. | WO | 99/40174 A1 | 8/1999 |
| 2007/0175756 | A1 | 8/2007 | Nguyen et al. | WO | 00/40712 A1 | 7/2000 |
| 2007/0184463 | A1 | 8/2007 | Molho et al. | WO | 00/60362 A1 | 10/2000 |
| 2007/0202531 | A1 | 8/2007 | Grover | WO | 00/61198 A1 | 10/2000 |
| 2007/0237686 | A1 | 10/2007 | Mathies et al. | WO | 00/72970 | 12/2000 |
| 2007/0238109 | A1 | 10/2007 | Min et al. | WO | 01/32930 A1 | 5/2001 |
| 2007/0248958 | A1 | 10/2007 | Jovanovich et al. | WO | 01/38865 A1 | 5/2001 |
| 2007/0297947 | A1 | 12/2007 | Sommers et al. | WO | 01/85341 A1 | 11/2001 |
| 2008/0014576 | A1 | 1/2008 | Jovanovich et al. | WO | 02/43615 A2 | 6/2002 |
| 2008/0014589 | A1 | 1/2008 | Link et al. | WO | 02/43615 A3 | 6/2002 |
| 2008/0047836 | A1 | 2/2008 | Strand et al. | WO | 02/43864 | 6/2002 |
| 2008/0124723 | A1 | 5/2008 | Dale et al. | WO | 03/085379 A2 | 10/2003 |
| 2008/0164155 | A1 | 7/2008 | Pease et al. | WO | 03/085379 A3 | 10/2003 |
| 2008/0179255 | A1 | 7/2008 | Jung et al. | WO | 2004/061085 | 7/2004 |
| 2008/0237146 | A1 | 10/2008 | Harrison et al. | WO | 2004/098757 A2 | 11/2004 |
| 2008/0281090 | A1 | 11/2008 | Lee et al. | WO | 2004/098757 A3 | 11/2004 |
| 2008/0302732 | A1 | 12/2008 | Soh et al. | WO | 2005/075081 A1 | 8/2005 |
| 2008/0311585 | A1 | 12/2008 | Gao et al. | WO | 2005/118867 | 12/2005 |
| 2009/0004494 | A1 | 1/2009 | Blenke et al. | WO | 2006/032044 | 3/2006 |
| 2009/0035770 | A1 | 2/2009 | Mathies et al. | WO | 2007/082480 A1 | 7/2007 |
| 2009/0053799 | A1 | 2/2009 | Chang-yen et al. | WO | 2007/109375 | 9/2007 |
| 2009/0056822 | A1 | 3/2009 | Young et al. | WO | 2008/039875 A1 | 4/2008 |
| 2009/0060797 | A1 | 3/2009 | Mathies et al. | WO | 2008/052138 | 5/2008 |
| 2009/0084679 | A1 | 4/2009 | Harrison et al. | WO | 2008/115626 A2 | 9/2008 |
| 2009/0134069 | A1 | 5/2009 | Handique | WO | 2008/115626 A3 | 9/2008 |
| 2009/0137413 | A1 | 5/2009 | Mehta et al. | WO | 2009/015296 | 1/2009 |
| 2009/0148933 | A1 | 6/2009 | Battrell et al. | WO | 2009/129415 A1 | 10/2009 |
| 2009/0181411 | A1 | 7/2009 | Battrell et al. | WO | 2010/041174 A1 | 4/2010 |
| 2009/0253181 | A1 | 10/2009 | Vangbo et al. | ZA | 2005/04838 | 3/2006 |
| 2009/0286327 | A1 | 11/2009 | Cho et al. | | | |
| 2009/0311804 | A1 | 12/2009 | Mcbrady et al. | | | |
| 2010/0068723 | A1 | 3/2010 | Jovanovich et al. | | | |
| 2010/0165784 | A1 | 7/2010 | Jovanovich et al. | | | |
| 2010/0224255 | A1 | 9/2010 | Mathies et al. | | | |
| 2010/0252123 | A1 | 10/2010 | Mathies et al. | | | |
| 2010/0303687 | A1 | 12/2010 | Blaga et al. | | | |
| 2010/0326826 | A1 | 12/2010 | Harrison et al. | | | |
| 2011/0005932 | A1 | 1/2011 | Jovanovich et al. | | | |
| 2011/0020920 | A1 | 1/2011 | Mathies et al. | | | |
| 2011/0027913 | A1 | 2/2011 | Bau et al. | | | |
| 2011/0039303 | A1 | 2/2011 | Jovanovich et al. | | | |
| 2011/0048945 | A1 | 3/2011 | Harrison et al. | | | |
| 2011/0076735 | A1 | 3/2011 | Jovanovich et al. | | | |
| 2012/0142010 | A1 | 6/2012 | Mathies et al. | | | |
| 2012/0164627 | A1* | 6/2012 | Battrell et al. ............... 435/5 | | | |
| 2012/0276544 | A1* | 11/2012 | Quake et al. ............... 435/6.12 | | | |

FOREIGN PATENT DOCUMENTS

| | | |
|---|---|---|
| CN | 102416350 | 4/2012 |
| EP | 0459241 B1 | 12/1991 |
| EP | 0637999 A1 | 2/1995 |
| EP | 0527905 B1 | 11/1995 |
| EP | 1065378 B1 | 4/2002 |
| EP | 1411340 A2 | 4/2004 |
| EP | 1411340 A3 | 4/2004 |
| EP | 1774042 | 4/2007 |
| EP | 1345697 B1 | 6/2007 |
| EP | 1658890 B1 | 5/2008 |
| EP | 2029921 | 3/2009 |
| EP | 1345551 B1 | 4/2009 |
| EP | 2404676 | 11/2012 |
| JP | 2007/506430 A | 7/1995 |
| JP | 408327594 A | 12/1996 |
| JP | 2001/500966 | 1/2001 |
| JP | 2001/521818 A | 11/2001 |
| JP | 2002/3701200 A | 12/2002 |

OTHER PUBLICATIONS

U.S. Appl. No. 12/820,390, filed Jun. 22, 2010, Harrison et al.
U.S. Appl. No. 12/845,650, filed Jul. 28, 2010, Jovanovich et al.
U.S. Appl. No. 12/949,623, filed Nov. 18, 2010, Kobrin et al.
Amendment and Request for Correction of Inventorship mailed Jan. 10, 2008 in U.S. Appl. No. 10/750,533.
Anderson, et al. A miniature integrated device for automated multistep genetic assays. Nucleic Acids Research. 2000;28:e60.
Bings, et al., "Microfluidic Devices Connected to Fused-Silica Capillaries with Minimal Dead Volume," Analytical Chemistry. 1999;71(15):3292-3296.
Blazej, et al. Microfabricated bioprocessor for integrated nanoliter-scale Sanger DNA sequencing. Proc. Natl. Acad. Sci. USA 2006;103:7240-7245.
Blazej, et al. Polymorphism Ratio Sequencing: A New Approach for Single Nucleotide Polymorphism Discovery and Genotyping. Genome Research. 2003;13:287-293.
Brenner, et al. Gene expression analysis by massively parallel signature sequencing (MPSS) on microbead arrays. Nature Biotechnology. 2000;18(6):630-634.
Buchholz, et al. The use of light scattering for precise characterization of polymers for DNA sequencing by capillary electrophoresis. Electrophoresis. 2001;22:4118-4128.
CAPLUS abstract of Krohkin et al. Modified silica as a stationary phase for ion chromatography. Journal of Chromatography A. 1995;706:93-8.
Chan, et al. Microfabricated Polymer Devices for Automated Sample Delivery of Peptides for Analysis by Electrospray Ionization Tandem Mass Spectrometry. Analytical Chemistry. 1999;71(20):4437-4444.
Chiem, et al. Microchip systems for immunoassay: an integrated immunoreactor with electrophoretic separation for serum theophylline determination. Clinical Chemistry.1998;44(3):591-598.

Chiem, et al. Room temperature bonding of micromachined glass devices for capillary electrophoresis. Sensors and Actuators. 2000;B63(3):147-152.

Coleman, et al. A sequential injection microfluidic mixing strategy. Microfluidics and Nanofluidics. 2005;319-327.

Curcio, et al. Continuous Segmented-Flow Polymerase Chain Reaction for High-Throughput Miniaturized DNA Amplification. Analytical Chemistry. 2003;75(1):1-7.

Diehl, et al. BEAMing: single-molecule PCR on microparticles in water-in-oil emulsions. Nature Methods. 2006;3(7):551-9.

Doiierty, et al. Sparsely Cross-linked "Nanogel" Matrices as Fluid, Mechanically Stabilized Polymer Networks for High-Throughput Microchannel DNA Sequencing. Analytical Chemistry. 2004;76:5249-5256.

Doherty, et al. Sparsely cross-linked "nanogels" for microchannel DNA sequencing. Electrophoresis. 2003;24(24):4170-4180.

Dorfman, et al. Contamination-Free Continuous Flow Microfluidic Polymerase Chain Reaction for Quantitative and Clinical Applications. Analytical Chemistry. 2005;77(11):3700-3704.

Doyle, et al. Self-Assembled Magnetic Matrices for DNA Separation Chips. Science. 2000;295:2237.

Dressman, et al. Transforming single DNA molecules into fluorescent magnetic particles for detection and enumeration of genetic variations. Proc Natl Acad Sci USA. 2003;100(15):8817-8822.

Ericson, et al. Electroosmosis- and Pressure-Driven Chromatography in Chips Using Continuous Beds. Analytical Chemistry. 2000;72(1):81-87.

Ewing, et al. Base-Calling of Automated Sequencer Traces Using Phred. I. Accuracy Assessment. Genome Research. 1998;8:175-185.

Ewing, et al. Base-Calling of Automated Sequencer Traces Using Phred. II. Error probabilities. Genome Research. 1998;8:186-194.

Figeys, et al. A Microfabricated Device for Rapid Protein Identification by Microelectrospray Ion Trap Mass Spectrometry. Analytical Chemistry. 1997;69(16):3153-3160.

Figeys, et al. An Integrated Microfluidics-Tandem Mass Spectrometry System for Automated Protein Analysis. Analytical Chemistry. 1998;70(18):3728-3734.

Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.

Figeys, et al. Nanoflow Solvent Gradient Delivery from a Microfabricated Device for Protein Identifications by Electrospray Ionization Mass Spectrometry. Analytical Chemistry. 1998;70(18):3721-3727.

Francis, et al. Flow analysis based on a pulsed flow of solution: theory, instrumentation and applications. Talanta. 2002;58(6):1029-1042.

Ghadessy, et al. Directed evolution of polymerase function by compartmentalized self-replication. Proc Natl Acad Sci USA. 2001;98:4552-4557.

Giddings, et al. A software system for data analysis in automated DNA sequencing. Genome Research. 1998;8:644-665.

Goll, et al. Microvalves with bistable buckled polymer diaphragms. Journal of Micromechanics and Microengineering. 1996;6:77-79.

Grover, et al. Development and multiplexed control of latching pneumatic valves using microfluidic logical structures. Lab on a chip. 2006;6:623-631.

Grover, et al. An integrated microfluidic processor for single nucleotide polymorphism-based DNA computing. Lab on a Chip. 2005;5(10):1033-1040.

Grover, et al. Monolithic Membrane Valves and Diaphragm pumps for Practical Large-Scale Integration into Glass Microfluidic Devices. 2003;89:315-323.

Grover, et al. Practical Valves and Pumps for Large-Scale Integration into Microfluidic Analysis Devices. Micro Total Analysis Systems. 2002;1:136-138.

Hansen, et al. A robust and scalable microfluidic metering method that allows protein crystal growth by free interface diffusion. Proc Natl Acad Sci USA. 2002;99(26):16531-16536.

Harrison, et al. Micromachining a Miniaturized Capillary Electrophoresis-Based Chemical Analysis System on a Chip. Science 1993;261; 895-897.

Hayes, et al. EDGE: A Centralized Resource for the Comparison, Analysis, and Distribution of Toxicogenomic Information. Molecular Pharmacology. 2005;67(4):1360-1368.

International Preliminary Report for corresponding PCT Application No. PCT/CA2000/01421 dated Feb. 14, 2002.

International Preliminary Report for corresponding PCT Application No. PCT/US2005/018678 dated Nov. 13, 2007.

International Preliminary Report for corresponding PCT Application No. PCT/US2005/033347 dated Mar. 20, 2007.

International Preliminary Report for corresponding PCT Application No. PCT/US2007/007381 dated Sep. 23, 2008.

International Preliminary Report for corresponding PCT Application No. PCT/US2007/02721 dated Aug. 5, 2008.

International Preliminary Report for corresponding PCT Application No. PCT/US2007/061573 dated Aug. 26, 2008.

International Search Report for PCT/US2005/033347 dated Aug. 23, 2006.

Ju, et al. Fluorescence energy transfer dye-labeled primers for DNA sequencing and analysis. Proc. Natl. Acad. Sci. USA. 1995;92:4347-4351.

Kan, et al. A novel thermogelling matrix for microchannel DNA sequencing based on poly-N-alkoxyalkylaclylamide copolymers. Electrophoresis. 2003;24(24):4161-4169.

Koh, et al. Integrating Polymerase Chain Reaction, Valving, and Electrophoresis in a Plastic Device for Bacterial Detection. Analytical Chemistry. 2003;75(17):4591-4598.

Kopp, et al. Chemical Amplification Continuous-Flow PCR on a Chip. Science. 1998;280:1046-1048.

Lagally, et al. Fully integrated PCR-capillary electrophoresis microsystem for DNA analysis. Lab on a Chip. 2001;1(2):102-107.

Lagally, et al. Integrated Portable Genetic Analysis Microsystem for Pathogen/Infectious Disease Detection. Analytical Chemistry. 2004;76:3162-3170.

Lagally, et al. Monolithic integrated microfluidic DNA amplification and capillary electrophoresis analysis system. Sensors and Actuators. 2000;B63(3):138-146.

Lagally, et al. Single-Molecule DNA Amplification and Analysis in an Integrated Microfluidic Device. Analytical Chemistry. 2001;73(3): 565-570.

Lazar, et al. Subattomole-Sensitivity Microchip Nanoelectrospray Source with Time-of-Flight Mass Spectrometry Detection. Analytical Chemistry. 1999;71(17):3627-3631.

Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.

Li, et al. Rapid and sensitive separation of trace level protein digests using microfabricated devices coupled to a quadrupole—time-of-flight mass spectrometer. Electrophoresis. 2000;21:198-210.

Li, et al. Separation and identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.

Licklider, et al. A Micromachined Chip-Based Electrospray Source for Mass Spectrometry. Analytical Chemistry. 2000;72(2):367-375.

Lisec, et al. A bistable pneumatic microswitch for driving fluidic components. Sensors and Actuators. 1996;A54:746-749.

Liu, et al. Automated parallel DNA sequencing on multiple channel microchips. Proc. Natl. Acad. Sci. USA. 2000;97(10):5369-5374.

Liu, et al. Optimization of High-Speed DNA Sequencing on Microfabricated Capillary Electrophoresis Channels. Analytical Chemistry. 1999;71:566-573.

Margulies, et al. Genome sequencing in microfabricated high-density picolitre reactors. Nature. 2005;437(7057):376-80. (Abstract only).

Melin, et al. A Passive 2-Dimensional Liquid Sample Micromixer. 7th International Conference on Miniaturized Chemical and Biochemical Analysis Systems. 2003;167-170.

Mitra, et al. Digital genotyping and haplotyping with polymerase colonies. Proc Nall Acad Sci USA. 2003.100(10):15926-5931.

Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.

Ocvirk, et al. High Performance Liquid Chromatography Partially Integrated onto a Silicon Chip. Analytical Methods and Instrumentation. 1995;2:74-82.

Ocvirk, et al. Optimization of confocal epifluorescence microscopy for microchip-based miniaturized total analysis systems. The Analyst. 1998;123:1429-1434.

Office Action Final dated Feb. 19, 2008 issued in U.S. Appl. No. 10/540,658.

Office Action Final dated Feb. 6, 2008 issued in U.S. Appl. No. 11/139,018.

Office Action mailed Apr. 27, 2007 in U.S. Appl. No. 11/139,018.

Office Action mailed Jul. 2, 2007 in U.S. Appl. No. 10/540,658.

Office Action mailed Jul. 12, 2007 in U.S. Appl. No. 10/750,533, filed Dec. 29, 2003.

Ohori, et al. Partly disposable three-way microvalve for a medical micro total analysis system (uTAS). Sensors and Actuators. 1998;A64(1): 57-62.

Oleschuk, et al. Trapping of Bead-Based Reagents within Microfluidic Systems: On-Chip Solid-Phase Extraction and Electrochromatography. Analytical Chemistry. 2000;72:585-590.

Olsen, et al. Immobilization of DNA Hydrogel Plugs in Microfluidic Channels. Analytical Chemistry. 2002;74:1436-1441.

Paegel, et al. High-throughput DNA sequencing with a 96-lane capillary array electrophoresis bioprocessor. Proc Natl Acad Sci USA. 2002;99:574-579.

Paegel, et al. Microchip Bioprocessor for Integrated Nanovolume Sample Purification and DNA Sequencing. Analytical Chemistry. 2002;74(19):5092-5098.

Paegel, et al. Microfluidic devices for DNA sequencing: sample preparation and electrophoretic analysis. Current Opinion in Biotechnology. 2003;14(1):42-50.

Paegel, et al. Turn Geometry for Minimizing Band Broadening in Microfabricated Capillary Electrophoresis Channels. Analytical Chemistry. 2000;72:3030-3037.

PCT Notification of Transmittal of the International Search Report and the Written Opinion of the International Searching Authority, or the Declaration, mailed Jun. 17, 2008, Application No. PCT/US2007/082568.

Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.

Ramsey, et al. Generating Electrospray from Microchip Devices Using Electroosmotic Pumping. Analytical Chemistry. 1997;69(6):1174-1178.

Rohr, et al. Porous polymer monoliths: Simple and efficient mixers prepared by direct polymerization in the channels of microfluidic chips. Electrophoresis. 2001;22:3959-3967.

Rye, et al. High-sensitivity two-color detection of double-stranded DNA with a confocal fluorescence gel scanner using ethidium homodimer and thiazole orange. Nucleic Acids Research. 1991;19(2):327-333.

Scherer, et al. High-Pressure Gel Loader for Capillary Array Electrophoresis Microchannel Plates. Biotechniques. 2001;31(5):1150-1154.

Sciiomburg, et al. Design Optimization of Bistable Microdiaphragm Valves. Sensors and Actuators. 1998;A64:259-264.

Seifar, et al. Capillary electrochromatography with 1.8-mum ODS-modified porous silica particles. Journal of Chromatography. 1998; A808:71-77.

Simpson, et al. High-throughput genetic analysis using microfabricated 96-sample capillary array electrophoresis microplates. Proc Nail Acad Sci USA. 1998;95:2256-2261.

Simpson, et al. Microfabrication Technology for the Production of Capillary Array Electrophoresis Chips. Biomedical Microdevices. 1998;1:7-26.

Soper, et al., "Sanger DNA Sequencing Reactions Performed in a Solid-Phase Nanoreactor Directly Coupled to Capillary Gel Electrophoresis," Analytical Chemistry, 1998, 70:4036-4043.

Spiering, et al. Novel microstructures and technologies applied in chemical analysis techniques. 1997 International Conference on Solid-State Sensors and Actuators. 1997;1:511-514.

Takao, et al. A Pneumatically Actuated Full In-Channel Microvalve With MOSFET-Like Function in Fluid Channel Networks. Journal of Microelectromechanical Systems. 2002;11(5):421-426.

Takao, et al. Microfluidic Integrated Circuits for Signal Processing Using Analogous Relationship Between Pneumatic Microvalve and MOSFET. Journal of Microelectromechanical Systems. 2003;12(4):497-505.

Thomas, et al. Application of Genomics to Toxicology Research. Environmental Health Perspectives. 2002;110(6):919-923.

Tice, et al. Formation of Droplets and Mixing in Multiphase Microfluidics at Low Values of the Reynolds and the Capillary Numbers. Langmuir. 2003;19:9127-9133.

Unger, et al. Monolithic Microfabricated Valves and Pumps by Multilayer Soft Lithography. Science. 2000;288:113-116.

Van Der Moolen, et al. A Micromachined Injection Device for CZE: Application to Correlation CZE. Analytical Chemistry. 1997;69(20):4220-4225.

Van Der Moolen, et al. Correlation Capillary Zone Electrophoresis, a Novel Technique to Decrease Detection Limits. Chromatographia. 1995;40(7/8):368-374.

Vazquez, et al. Electrophoretic Injection within Microdevices. Analytical Chemistry. 2002;74:1952-1961.

Veenstra, et al. The design of an in-plane compliance structure for microfluidical systems. Sensors and Actuators. 2002;B81:377-383.

Waller, et al. Quantitative Immunocapture PCR Assay for Detection of Campylobacter jejuni in Foods. Applied Environmental Microbiology. 2000; 66(9):4115-4118.

Weimer, et al. Solid-Phase Capture of Proteins, Spores, and Bacteria. Applied Environmental Microbiology. 2001;67(3):1300-1307.

Wen, et al. Microfabricated isoelectric focusing device for direct electrospray ionization-mass spectrometry. Electrophoresis. 2000;21:191-197.

Wikipedia brochure for defining stocahstic process. Sep. 2, 2009.

Williams, et al. Amplification of complex gene libraries by emulsion PCR. Nature Methods. 2006;3(7):545-50.

Woolley, et al. Functional Integration of PCR Amplification and Capillary Electrophoresis in a Microfabricated DNA Analysis Device. Analytical Chemistry. 1996;68(23):4081-4086.

Wright, et al. Behavior and Use of Nonaqueous Media without Supporting Electrolyte in Capillary Electrophoresis and Capillary Electrochromatography. Analytical Chemistry. 1997;69(16):3251-3259.

Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.

Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.

Xue, et al. Multichannel Microchip Electrospray Mass Spectrometry. Analytical Chemistry. 1997;69(3):426-430.

Yang, et al. A MEMS thermopneumatic silicone rubber membrane valve. Sensors and Actuators. 1998;A64(1):101-108.

Yu, et al. Preparation of Monolithic Polymers with Controlled Porous Properties for Microfluidic Chip Applications Using Photoinitiated Free Radial Polymerization. Journal of Polymer Science. 2002;40:755-769.

Yu, et al. Towards stationary phases for chromatography on a microchip: Molded porous polymer monoliths prepared in capillaries by photoinitiated in situ polymerization as separation media for electrochromatogaphy. Electrophoresis. 2000;21:120-127.

Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.

Zhang, et al. Microfabricated Devices for Capillary Electrophoresis-Electrospray Mass Spectrometry. Analytical Chemistry. 1999;71(15):3258-3264.

Chinese Office Action dated Jan. 25, 2008, from Application No. 2003801100666.
Hultman, T.S., et al. Bidirectional Solid-Phase Sequencing of in Vitro-Amplified Plasmid DNA. Bio Techniques, 1991. 10:p. 84-93.
Nakano, H., et al., "Single-Step Single-Molecule PCR of DNA with a Homo-Priming Sequence Using a Single Primer and Hot-Startable DNA Polymerase," Journal of Bioscience and Bioengineering, 2000, vol. 90:4, pp. 456-458.
Leamon, J.H., et al., A massively parallel Pico Titer Plate (TM) based platform for discrete picoliter-scale polymerase chain reactions, Electrophoresis, 2003, vol. 24, pp. 3769-3777.
Ghadessy, F.J., et al., "Directed evolution of polymerase function by compartmentalized self-replication," PNAS, 2001, vol. 98, pp. 4552-4557.
Fleming, et al., "LD-PCR coupled to long-read direct sequencing: an approach for mutation detection in genes with compact genomic structures," Journal of Biochemical and Biophysical Methods, 2001, vol. 47:1-2, pp. 131-136.
Kamei, T., et al., "Integrated Hydrogenated Amorphous Si Photodiode Detector for Microfluidic Bioanalytical Devices," Analytical Chemistry, 2003, vol. 75, pp. 5300-5305.
Albarghouthi, M.N., "Poly-N-hydroxyethylacrylamide (polyDuramide): A novel hydrophilic self-coating polymer matrix for DNA sequencing by capillary electropfiroesis," Electrophoresis, 2002. vol. 23, pp. 1429-1440.
Song, H., et al., "A microfluidic system for controlling reaction networks in time," Angewandte Chemie-International Edition 42, 2003. pp. 768-772.
Srinivasan, U., et al., "Alkyltrichlorosilane-based self-assembled monolayer films for stiction reduction in silicon micromachines," Journal of Microelectromechanical Systems, 1998, vol. 7, pp. 252-260.
Thorsen et al., "Microfluidic Large-Scale Integration", Science, vol. 298, Oct. 18, 2002, pp. 580-584.
Park, Nokyoung, et al., "Cylindrical Compact Thermal-Cycling Device for Continuous-Flow Polymerase Chain Reaction," Anal. Chem., Nov. 1, 2003, vol. 75, No. 21, pp. 6029-6033.
Emrich et al., "Microfabricated 384-lane capillary array electrophoresis bioanalyzcr for ultrahigh-throughput genetic analysis," Analytical Chemistry, 2002, vol. 74:19, pp. 5076-5083.
Mathies, R.A., et al., "Capillary array electrophoresis bioprocessors, Solid-State Sensor," Actuator and Microsystems Workshop, 2002, pp. 112-117, Hilton Head Island, SC, USA.
Ligler, F.S., et al., "Integrating Waveguide Biosensor," Anal. Chem., 2002, vol. 74, pp. 713-719.
Notice of Allowance and Fees Due mailed Aug. 13, 2008 from U.S. Appl. No. 10/750,533.
Office Action dated Oct. 8, 2008 issued in U.S. Appl. No. 10/540,658.
Office Action Final dated Mar. 2, 2009 issued in U.S. Appl. No. 10/540,658.
International Search Report and the Written Opinion of the International Searching Report Oct. 29, 2007, Application No. PCT/US2005/018678.
Mathies, et al., U.S. Appl. No. 10/750,533, titled "Fluid Control Structures in Microfluidic Devices," filed Dec. 29, 2003.
Mathies, et al., U.S. Appl. No. 12/203,800, titled "Fluid Control Structures in Microfluidic Devices," filed Sep. 3, 2008.
Mathtes, et al., U.S. Appl. No. 10/540,658, titled "Methods and Apparatus for Pathogen Detection and Analysis," filed Jun. 23, 2005.
Mathies, et al., U.S. Appl. No. 11/139,018, titled "Microfabricated Integrated DNA Analysis System," filed May 25, 2005.
Mathies, et al., U.S. Appl. No. 11/726,701, titled "Multiplexed Latching Valves for Microfluidic Devices and Processors," filed Mar. 21, 2007.
Office Action Final dated Aug. 27, 2008 issued in U.S. Appl. No. 11/139,018.
Office Action Final dated Apr. 29, 2009 issued in U.S. Appl. No. 11/139,018.
PCT Notification of Transmittal of the International Search Report and the Written Opinion of the International Searching Authority, or the Declaration, mailed Jul. 15, 2008, Application No. PCT/US2007/007381.
Hidekuni, T., et al. A Pneumatically Actuated Full in Channel Microvalve With MOSFET-Like Function IN Fluid Channel Networks, Journal of Microelectromechanical Systems, 2002, 11:5; 421-426. P066).
Hidekuni, T., et al., Microfluidic Integrated Circuits for Signal Processing Using Analogous Relationship Between Pneumatic Microvalve and MOSFET, Journal of Microelectromechanical System 2003, 12:4; 497-505.
Mircea, C., et al., Design Fabrication and Testing of a Bistable Electromagnetically Actuated Microvalve. Journal of Microeclectromechanical System 2000. vol. 9; 181-189.
Roth, C. et al., Fundamentals of Logic Design, $3^{rd}$ Edition, West Publishing Company, 1985 (Table of Content).
Press, W., et al., The Art of Scientific Computing, Numerical Recipes in C, 2nd Edition, Cambridge University Press, 1992, (table of Contents).
Office Action Final dated Dec. 11, 2009 issued in U.S. Appl. No. 11/726,701.
Office Action Final dated Nov. 6, 2009 issued in U.S. Appl. No. 11/139,018.
Office Action Final dated Feb. 22, 2010 issued in U.S. Appl. No. 11/139,018.
Notice of Allowance for U.S. Appl. No. 11/139,018 mailed Jul. 1, 2010.
Mathies, et al., U.S. Appl. No. 12/782,598, titled "Fluid Control Structures in Microfluidic Devices," filed May 18, 2010.
Chinese Office Action Final dated Feb. 24, 2010 issued Appl. No. 200780018073.1.
Notice of Allowance and Fees Due mailed May 6, 2010 from U.S. Appl. No. 11/726,701.
Allowed Claims from U.S. Appl. No. 11/726,701.
Blazej, et al., Inline Injection Microdevice for Attomole-Scale Sanger DNA Sequencing, Anal. Chem., 2007, 79(12), pp. 4499-2506.
Mathies, et al., U.S. Appl. No. 12/844,544, titled "Microfabricated Integrated DNA Analysis System," filed Jul. 27, 2010.
Japanese Office Action dated Jan. 13, 2010, from Application No. 2005-508628.
Japanese Office Action dated Aug. 10, 2010, from Application No. 2005-508628.
European Supplemental Search Report dated Sep. 1, 2010 from Application No. 05804847.1.
Hjerten, High-Perfoll lance Electrophoresis: Elimination of Electronendosmosis and Solute Adsorption, J. Chromotography, 347, 1985, pp. 191-198.
Mathies, et al., U.S. Appl. No. 11/978,224, titled "Inline-Injection Microdevice and Microfabricated Integrated DNA Analysis System Using Same," filed Oct. 25, 2007.
Office Action Final dated Jan. 20, 2010 issued in U.S. Appl. No. 11/978,224.
Office Action dated Oct. 25, 2010 issued in U.S. Appl. No. 11/978,224.
Hartmann, A., et al., "Direct immobilization of Antibodies on Phthalocyaninato-polysiloxane Photopolymers," Thin Solid Films, 245, 1994, pp. 206-210.
Hartmann, A., et al., One-Step Immobilization of Immunoglobulin G and Potential of the Method for Application in Immunosensors, Sensors and Actuators 28 (2), 1995, pp. 143-149.
Sanford, et al., "Photoactivatable Cross-Linked Polyacrylamide for the Site-Selective Immobilization of Antigens and Antibodies," Chem Mater., 1998, vol. 10, No. 6, pp. 1510-1520.
Office Action mailed Jan. 7, 2011 from U.S. Appl. No. 12/844,544.
Notification of Provisional Rejection received Jan. 8, 2011, in Application No. 2005-7012095.
Yu, Cong, et al., "Towards Stationary Phases for Chromatography on a Microchip: Molded Porous Polymer Monoliths Prepared in Capillaries by Photoinitiated in situ Polymerization as Separation Media for Electrochromatography," Electrophoresis 2000, vol. 21, pp. 120-127.
Request for Ex Parte Reexamination of U.S. Patent No. 7,445,926.
Hosokawa, et al., "A Pneumatically-Actuated Three-Way Microvalve Fabricated with Polydimethylsiloxane Using the Membrane Transfer Technique," J. Micrormech. Microeng., vol. 10, 2000, pp. 415-420.

Mathies, et al., U.S. Appl. No. 12/819,094, titled "Multiplexed Latching Valves for Microfluidic Devices and Processors," filed Jun. 18, 2010.
Japanese Office Action mailed Mar. 1, 2011 for Appln. No. 2007-515379.
European Office Action mailed Apr. 7, 2011 from Application No. 05804847.1.
International search report and written opinion dated Mar. 24, 2011 for PCT Application No. US2010/58227.
International search report and written opinion dated Sep. 1, 2010 for PCT Application No. US2010/040490.
International search report dated Oct. 6, 2010 for PCT Application No. US10/37545.
International search report dated Apr. 5, 2001 for PCT Application No. CA2000/01421.
International search report dated May 14, 2010 for PCT Application No. US2009/06640.
International search report dated Jul. 11, 2008 for PCT Application No. US07/61573.
International search report dated Jul. 30, 2010 for PCT Application No. US2010/36464.
International search report dated Aug. 18, 2009 for PCT Application No. US09/00419.
International search report dated Aug. 26, 2004 PCT Application No. US2003/41466.
International search report dated Sep. 25, 2007 for PCT Application No. US2007/02721.
Jacobson, et al. Electrokinetic Focusing in Microfabricated Channel Structures. Anal. Chem., 1997, 69 (16), pp. 3212-3217.
Japanese Office Action dated Dec. 21, 2010 for Application No. JP2001-540363 (in Japanese with English translation).
Japanese Office Action dated Apr. 27, 2010 for Application No. JP2001-540363 (in Japanese with English translation).
MillGat pump user manual, version 2.12, published 2005, pp. 1-28.
Norris, et al. Fully-integrated, multiplexed STR-based human identification using a single microfluidic chip and automated instrument. Available at http://www.promega.com/geneticidproc/ussymp20proc/oralpresentations/landersbienvenue.pdf . Accessed Jun. 2, 2010.
European Supplemental International Search Report dated Dec. 18, 2009.
Kamel, T., et al., "Integrated Hydrogenated Amorphous Si Photodiode Detector for Microfluidic Bioanalytical Devices," Analytical Chemistry, 2003, vol. 75, pp. 5300-5305.
Koch, et al. "Optical flow cell multichannel immunosensor for the detection of biological warefare agents" Biosensors & Bioelectrics 14 (2000) pp. 779-784.
Yacoub-George, et al. "Chemiluminescence multichannel immunosensor for biodetection" Analytica Chimica Acta 457 (2002) pp. 3-12.
Delehanty, et al. "A Microarray Immunoassay for Simultaneous Detection of Proteins and Bacteria" Anal. Chem. 2002, 74, pp. 5681-5687.
Rowe-Taitt, et al., "Simultaneous detection of six biohazardous agents using a planar waveguicle array biosensor", Biosensors & Bioelectronics 15 (2000) pp. 5798-589.
Rowe, et al., "Array Biosensor for Simultaneous Identification of Bacterial, Viral and Protein Analytes" Anal. Chem. 1999, 71 pp. 3846-3852.
O'Mahony, et al. "A real time PCR assay for the detection and quantitation of *Mycobacterium avium* subsp. Paratuberculosis using SYBR Green and the Light Cycler" Journal of Microbiological Methods 51 (2002) pp. 283-293.
Papadelli, et al., "Rapid detection and identification of *Streptococcus macedonicus* by species-specific PCR and DNA hybridisation" International Journal of Food Microbiology 81 (2003) pp. 231-239.
Hansen, et al. "Polymerase chain reaction assay for the detection of *Bacillus cereus* group cells" FEMS Microbiology Letters 202 (2001) pp. 209-213.
Kong, et al." Rapid detection of six types of bacterial pathogens in marine waters by multiplex PCR" Walter Research 36 (2002) pp. 2802-2812.

Nataro, et al. "Diarrheagenic *Escherichia coli*" Clinical MicroBiology Reviews, Jan. 1998 pp. 142-201.
Kimura, et al. Restriction-Site-Specific PCR as a Rapid Test to Detect Enterohemorrhagic *Escherichia coli* O157:H7 Strains in Environmental Samples; Applied and Environmental Microbiology Jun. 2000 (pp. 2513-2519).
Peng, et al. "Immuno-capture PCR for detection of *Aeromonas hydrophila*" Journal of Microbiological Methods 49 (2002) pp. 335-338.
Call, et al. "Detecting and genotyping *Escherichia coli* O157:H7 using multiplexed PCR and nucleic acid microarrays" International Journal of Food Microbiology 67 (2001) pp. 71-80.
White, et al., "Flash detection/identification of pathogens, bacterial spores and bioterrorism agent biomarker from clinical and environmental matrices" Journal of Microbiological Methods 48 (2002) pp. 139-147.
Ruan, et al. "Immunobiosensor Chips for Detection of *Escherichia coli* O157:H7 Using Electrochemical Impedance Spectroscopy" Anal. Chem 2002 74 pp. 4814-4820.
Gau, et al., "A MEMS based amperometric detector for *E. Coli* bacteria using self-assembled monolayers" Biosensors & Bioelectronics 16 (2001) pp. 745-755.
Kourentzi, et al., "Microbial identification by immunohybridization assay of artificial RNA labels" Journal of Microbiological Methods 49 (2002) pp. 301-306.
Belgrader, et al. "Rapid PCR for Identity Testing Using a Battery-Powered Miniature Thermal Cycler" J Forensic Sci. 1998, pp. 315-319.
Belgrader, et al. "A Minisonicator to Rapidly Disrupt Bacterial Spores for DNA Analysis" Anal. Chem 1999 pp. 4232-4236.
Belgrader, et al. "PCR Detection of Bacteria in Seven Minutes" Science Magazine vol. 284, Issue 5413 (1999) pp. 449-450.
Verlee, et al. "Fluid Circuit Technology: Integrated Interconnect Technology for Miniature Fluidic Devices" Abbott Laboratories Hospital Division, Abbott Park, IL (1996) pp. 9-14.
Dodson, et al., "Fluidics Cube for Biosensor Miniaturization" Anal. Chem 2001 pp. 3776-3780.
Walt, et al., "Biological Warefare" Analytical Chemistry (2000) pp. 739-746.
Yang, et al. "An Integrated Stacked Microlaboratory for Biological Agent Detection with DNA and Immunoassays" Bioscnsors & Biocicctronics 17 (2002) pp. 605-618.
Reyes, et al. "Micro Total Analysis Systems. 1. Introduction Theory and Technology" Anal Chem (2002) pp. 2623-2636.
Auroux, et al. "Micro Total Analysis Systems 2. Analytical Standard Operations and Applications" Anal. Chem 2002 pp. 2637-2652.
Manz, et al. "Miniaturized Total Chemical Analysis Systems: A Novel Concept for Chemical Sensing" Sensors & Actuators (1990) pp. 244-248.
Jacobson, et al. "High-Speed Separations on a Microchip" Anal. Chem 1994 pp. 1114-1118.
Soper, et al. "Polymeric Microelectro-mechanical Systems" Anal. Chem (2000) pp. 643-651.
Shi, et al. "Radial Capillary Array Electrophoresis Microplate and Scanner for High Performance Nucleic Acid Analysis" Anal. Chem 1999 pp. 5354-5361.
Waters, et al. "Microchip Device for Cell Lysis, Multiplex PCR Amplification, and Electrophoretic Sizing" Anal. Chem 1999 pp. 158-162.
Jacobson, et al. "Integrated Microdevice for DNA Restriction Fragment Analysis" Anal. Chem 1996 pp. 720-723.
Burns, et al. "An Integrated Nanoliter DBA Analysis Device" Science Magazine 1998 pp. 484-487.
Duffy, et al. "Rapid Prototyping of Microfluidic Systems in Poly(dimethylsiloxane)" Anal. Chem 1998 (pp. 4974-4984.
Quake, et al. "From Micro-to Nanofabrication with Soft Materials" Science Magazine (2000) pp. 1536-1540.
Medintz, et al. "High-Performance Genetic Analysis Using Microfabricated Capillary Array Electroporesis Microplates" Electrophoresis 2001 pp. 3845-3856.
Medintz, et al. "High-Performance Multiplex SNP Analysis of Three Hemochmromatosis-Related Mutations with Capillary Array Electrophoresis Microplates" Genome Research 2001 pp. 413-421.

Medintz, et al. "Genotyping Energy-Transfer Cassette Labeled Short Tandem Repeat Amplicons with Capillary Array Electrophoresis Microchannel Plates" Clinical Chemistry (2001) pp. 1614-1621.

Webster, et al. "Monolithic Capillary Electrophoresis Device with Integrated Fluorescence Detector" Anal. Chem 2001 pp. 1622-1626.

Kamel, et al. "Integrated Amorphous Silicon Photodiode Detector for Microfabricated Capillary Electrophoresis Devices" Micro Total Analysis Systems 2002 pp. 257-259.

Kuhnert, et al. "Detection System for *Escherichia coli*-Specific Virulence Genes: Absence of Virulence Determinants in B and C Strains" applied and Environmental Microbiology (1997) pp. 703-709.

Stumpfle, et al. "Absence of DNA sequence homology with genes of the *Excherichia coli* hemB locus in Shiga-toxin producing *E. coli* (STEC) 0157 Strains" FEMS Microbiology Letters 174 (1999) pp. 97-103.

Chandler, et al. "Automated immunomagnetic separation and microarray detection of *E. coli* 0157:H7 from poultry carcass rinse" International Journal of Food Microbiology 70 (2001) pp. 143-154.

Tian, et al. "Evaluation of Silica Resins for Direct and Efficient Extraction of DNA from Complex Biological Matrices in a Miniaturized Format" Analytical Biochemistry 283 (2000) pp. 175-191.

He, et al. "Fabrication of Nanocolumns for Liquid Chromatography" Anal. Chem 1998 pp. 3790-3797.

Birnmoim, H.C. "A Rapid Alkaline Extraction Method for the Isolation of Plasmid DNA" Methods of Enzymology vol. 100 (1983) pp. 243-255.

Zhu, et al., "High-Sensitivity Capillary Electrophoresis of Double-Stranded DNA Fragments Using Monomeric and Dimeric Fluorescent Intercalating Dyes" Anal Chem 1994 pp. 1941-1948.

Medintz, et al. "Novel Energy Transfer Fluorescence Labeling Cassette" BioTechniques vol. 32 No. 2 (2002) p. 270.

Sun, et al. "A Heater-Integrated Transparent Microchannel Chip for Continuous Flow PCR" Sensors and Actuators B 84 (2002) pp. 283-289.

PCT International Search Report dated Aug. 26, 2004, Application No. PCT/US03/41466.

Canadian Office Action dated Jun. 10, 2011, Application No. 2,512,071.

Notification of Provisional Rejection mailed Oct. 21, 2011 for Application No. 2006-7026091.

Final Office Action mailed Sep. 12, 2011 from U.S. Appl. No. 12/844,544.

Final Office Action Final dated Jul. 8, 2011 issued in U.S. Appl. No. 11/978,224.

Chinese Office Action mailed Oct. 9, 2011, in Application No. 200910160476.0.

Chinese Notice of Amendment issued Aug. 30, 2011 for Appl. No. 201110197721.2.

Office Action Final dated Feb. 8, 2012 issued in U.S. Appl. No. 12/203,800.

Korean Office Action mailed Oct. 11, 2011, for Application No. 2011-7015771.

Office Action Final dated Feb. 24, 2012 issued in U.S. Appl. No. 12/819,094.

Office Action dated Apr. 12, 2012 issued in U.S. Appl. No. 13/372,376.

Notice of Allowance mailed Jun. 8, 2012 for U.S. Appl. No. 12/819,094.

Final Office Action dated Jul. 13, 2012 issued in U.S. Appl. No. 12/203,800.

Japanese Office Action mailed Sep. 4, 2012 for Application No. 2011-155300.

Japanese Decision on Rejection mailed Apr. 3, 2012 for Application No. 2007-515379.

European Office Action mailed Oct. 23, 2012 from Application No. 05804847.1.

Japanese Decision of Rejection dated Mar. 15, 2011, from Application No. 2005-508628.

International Search Report mailed Oct. 10, 2008 issued in PCT/US2008/071086.

\* cited by examiner

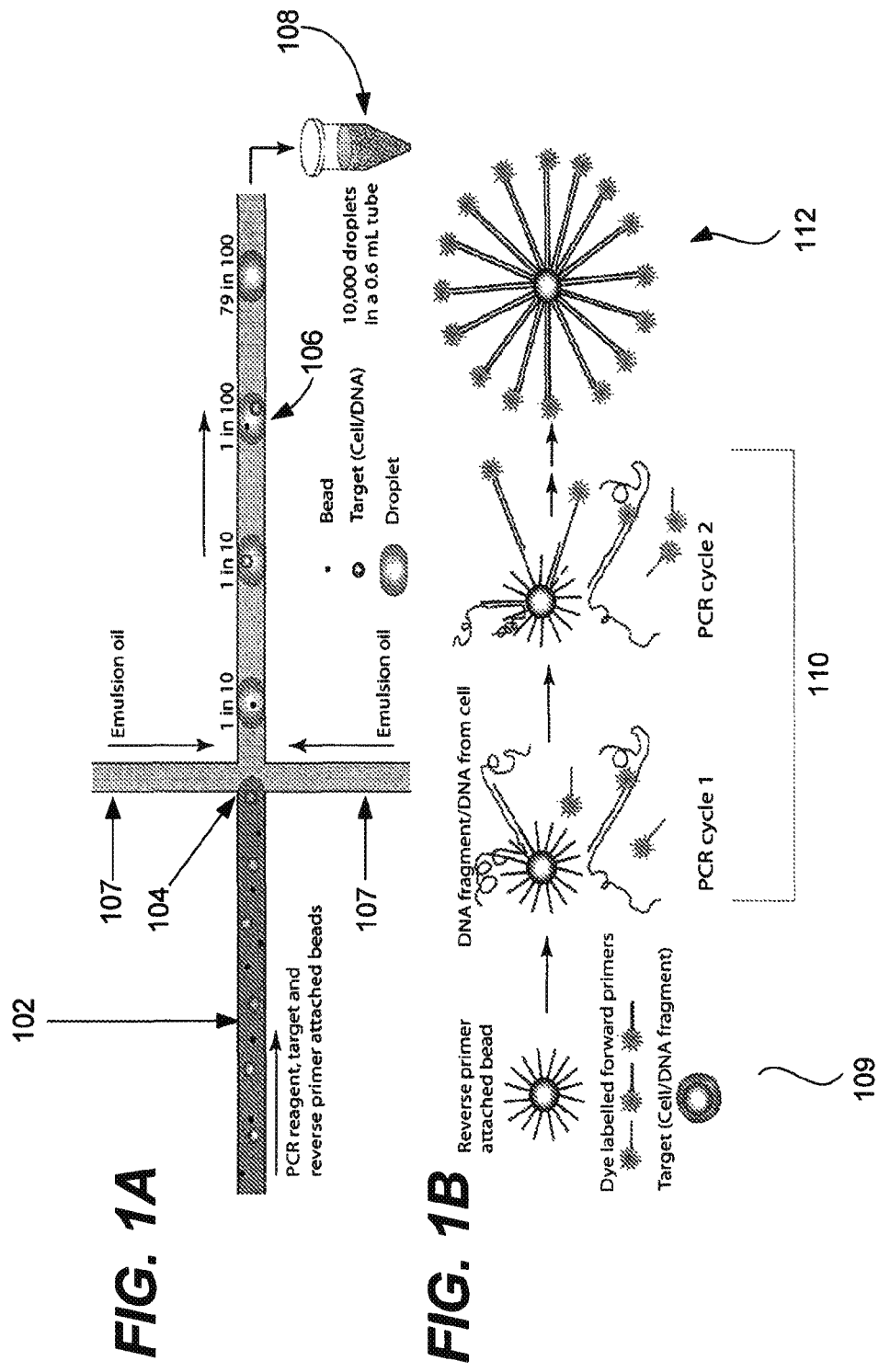

FIG. 3E
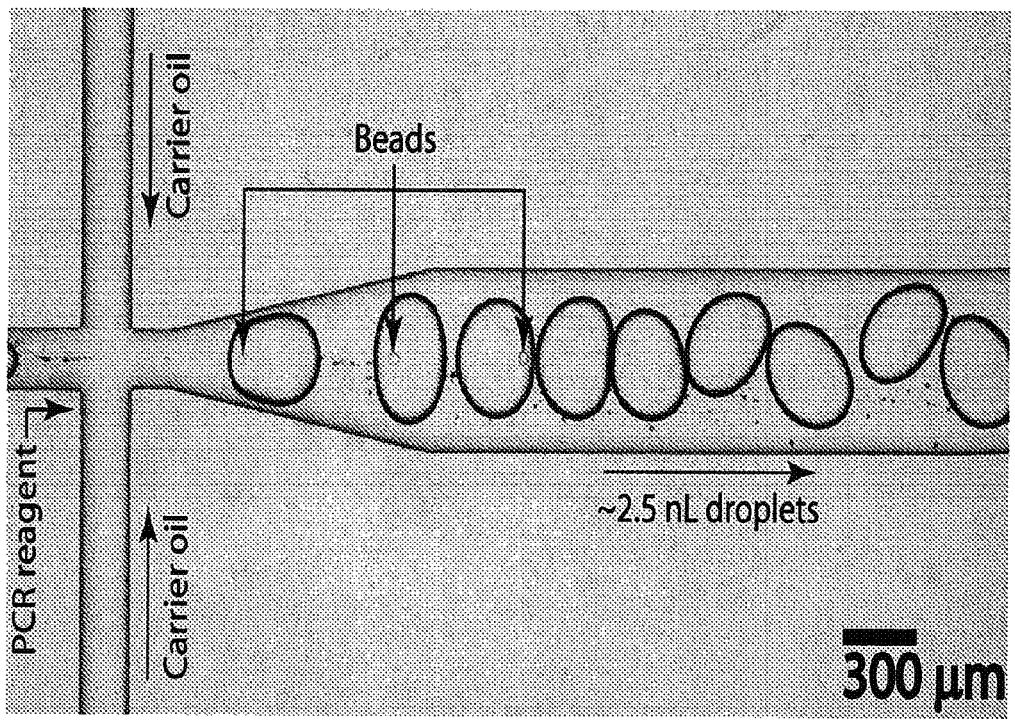
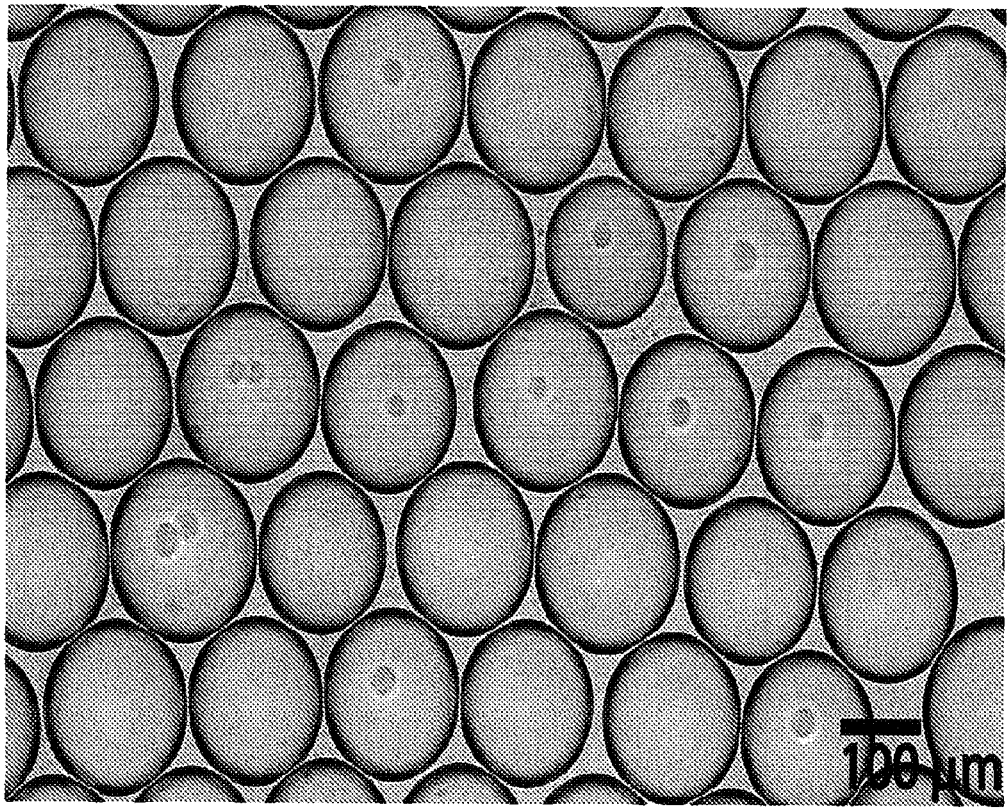
FIG. 3F

US 8,454,906 B2

MICROFABRICATED DROPLET GENERATOR FOR SINGLE MOLECULE/CELL GENETIC ANALYSIS IN ENGINEERED MONODISPERSED EMULSIONS

CROSS REFERENCE TO RELATED APPLICATIONS

This application claims priority under 35 U.S.C. 119(e) from Provisional U.S. Patent Application Ser. No. 60/961,926, filed Jul. 24, 2007 and from Patent Application Ser. No. 60/962,059, filed Jul. 25, 2007, both titled "MICROFABRICATED DROPLET GENERATOR FOR SINGLE MOLECULE/CELL GENETIC ANALYSIS IN ENGINEERED, MONODISPERSED EMULSIONS," which are incorporated herein by reference in their entireties.

STATEMENT REGARDING GOVERNMENT SUPPORT

This invention was made with government support under Grant No. HG003583 awarded by the National Institutes of Health. The government has certain rights in this invention.

BACKGROUND

1. Field of Invention

The invention relates to generation of micro-fluid droplets, e.g., for genetic analysis.

2. Description of Related Art

Sanger sequencing has improved greatly over the past 15 years but more significant advances are possible. Sanger sequencing was dramatically advanced by the transition to capillary array electrophoresis technologies. The utility of this separation method was also enhanced by the introduction of Energy Transfer (aka Big Dye) labels for the sequencing primers and terminators to enhance fluorescence signal strengths and reduce cross talk. These improvements in the labeling and separation coupled with many improvements in the other aspects of Sanger sequencing, facilitated the sequencing of the human genome and evolved the sequencing process to a relatively low cost and stable paradigm. However, this cost and production process is not sufficiently cheap or efficient to enable the routine sequencing or resequencing of a mammalian genome, so efforts are underway to reduce this cost. The injection of extension fragments into the capillary by conventional methods is only 1-0.1% efficient, wasting nearly all of the fluorescently labeled product because of the injection geometry. The current cloning, PCR or RCA sample preparation methods produce many orders of magnitude more template than is necessary and this scale requires the use of large space-demanding robotic transfer systems. The cloning/template amplification part of Sanger sequencing has not improved fundamentally since the start of the genome project.

Blazej et al. recently developed a sequencing microprocessor that performs thermal cycling of template in a 200 nL reactor. (*Microfabricated bioprocessor for integrated nanoliter-scale Sanger DNA sequencing*. Proc. Natl. Acad. Sci. U.S.A. 2006, 103, 7240-7245), incorporated by reference herein. The sequencing extension products are cleaned up on a microfabricated chip by electrophoresing them through a gel carrying a covalently attached oligonucleotide capture probe that selectively binds only the extension fragments. Electrophoretic "washing" eliminates excess salts, nucleotides and fluorescent labels. The products are released by raising the temperature of the device to the sequencing temperature which released the products for a cross channel injection. Using this method high quality sequencing data was obtained from only 1 femtomole of template. The efficiency is improved by placing the capture gel "in-line" with the separation column. See U.S. patent application Ser. No. 11/978,224, filed Oct. 25, 2007 and titled Inline-Injection Microdevice And Microfabricated Integrated Dna Analysis System Using Same, incorporated by reference herein. In this case, all of the extended fragments are captured within the separation column; subsequent thermal release provides 100% injection efficiency. This device produces high quality Sanger separations from only 100 attomoles of template.

Conventional methods, however, of PCR amplification do not allow single cell amplification to produce a uniform amount of template. Current "shake and bake" methods of generating emulsion droplets containing reactants (e.g., via agitation) produce polydisperse droplets, having a wide range of sizes and containing widely varying amounts of target and reagent.

SUMMARY

Provided are microfluidic designs and methods for rapid generation of engineered, monodisperse (i.e., uniform-size) picoliter to nanoliter volume droplets of reagent/target (molecule or cell) mix in emulsion oil. The designs and methods enable high-throughput encapsulation of a single target (e.g., DNA/RNA molecules or cells) in controlled size droplets of reagent mix. According to various embodiments, a microfabricated, 3-valve pump is used to precisely meter the volume of reagent/target mix in each droplet and also to effectively route microparticles such as beads and cells into the device, which are encapsulated within droplets at the intersection of a reagent channel and an oil channel. The pulsatile flow profile of the microfabricated pump provides active control over droplet generation, thereby enabling droplet formation with oils that are compatible with biological reactions but are otherwise difficult to form emulsions with. Applications include various genetic and gene expression analyses, combining the advantages of efficient single-molecule amplification in picoliter or nanoliter-volume engineered emulsions and effective product transfer using primer functionalized bead encapsulation.

One aspect of the invention provides microfluidic designs and methods for rapid generation of engineered, monodisperse picoliter or nanoliter volume droplets of PCR mix in emulsion oil. The designs and methods enable high-throughput encapsulation of a single primer functionalized microbead and a single target (e.g., DNA/RNA molecules or cells) in controlled size droplets of PCR mix.

Another aspect of the invention relates to a microdroplet generator including a micropump configured to precisely meter picoliter or nanoliter-volume droplets of reagent mixture. According to various embodiments, the generator includes a reagent inlet to a reagent channel, a plurality of oil inlets to an oil channel, a pneumatic layer including a plurality of pneumatic channels, a first fluidic layer including the reagent channel, an elastomeric layer sandwiched between the pneumatic layer and the first fluidic layer, a three-valve pump formed by valve displacements in the plurality of pneumatic channels aligned with discontinuities in a reagent channel, the pump configured to provide pulsatile flow of reagent from the reagent inlet to a nozzle via the reagent channel; the nozzle is formed by a junction of the reagent channel and the oil channel and is configured to form monodisperse emulsion droplets.

The reagent channels in the first fluidics layers are glass-elastomer hybrid channels, with the etched channels in the fluidics layer facing the elastomer. In certain embodiments, the generator also includes a second fluidic layer, which includes the oil channels and nozzle. A via connects the glass-elastomer hybrid channel to all-glass reagent channels in the second fluidics layer. In other embodiments, the oil channels and nozzle are part of the first fluidics layer.

According to various embodiments, the three-valve pump forms monodisperse (uniform size) pulses of reagent mixture of volume ranging from about 100 pL to 10 nL. The microvalve pump can form monodisperse droplets at frequencies as high as 50 Hz to 100 Hz.

In another implementation, a microfabricated structure having a microfabricated glass fluidic layer including an etched reagent channel; a microfabricated glass manifold layer with etched pneumatic channels; an elastomeric membrane sandwiched between the fluidic layer and the manifold layer; a glass-elastomer-glass pneumatically controlled micropump integrated on the microfabricated structure, said micropump configured to meter picoliter or nanoliter-volume droplets of reagent; a glass wafer comprising an all-glass reagent channel, an all-glass oil channel and a cross-injector configured to from picoliter or nanoliter-volume oil emulsion droplets of reagent; and a via hole connecting the etched reagent channel to an all-glass channel in the glass wafer is provided.

In another implementation, an arrayed microdroplet generator is provided. The generator includes a reagent inlet connected to a plurality of glass-elastomeric hybrid reagent channels; a plurality of three-valve elastomeric valves configured to produce pulsatile flow of reagent mix in the plurality of glass-elastomeric hybrid channels and pump the flow to a plurality of nozzles; a pneumatic layer having a plurality of pneumatic lines configured to simultaneously control the three-valve pumps; and a plurality of oil channels connected to a plurality of nozzles, the plurality of nozzles configured to produce monodisperse emulsion droplets and flow said emulsion droplets to a plurality of outputs.

Another aspect of the invention relates to a method of generating microdroplets. The method involves providing a reagent and target mixture to a reagent inlet channel on a microfabricated structure; forming droplets of the mixture in the channel via an in-channel three-valve elastomeric pump, wherein the pumping frequency and the droplet formation frequency have a 1:1 correspondence; and routing the droplets to a nozzle to form monodisperse emulsion droplets encapsulating reagent and targets. In certain embodiments, no more than a single target is encapsulated in a sufficiently high percentage of emulsion droplets. Also in certain embodiments, the reagent and target mixture further includes a microcarrier element such as a microbead. For example, the reagent and target mixture includes PCR reagent, primer functionalized microcarrier elements, and target. In other embodiments, a bead or other microcarrier element is functionalized with antibodies for cell capture using antibody-antigen interactions.

Yet another aspect of the invention relates to a method of amplifying genetic material involving providing a mixture comprising PCR reagent, primer-functionalized microbeads and target molecules or cells to a reagent inlet channel on a microfabricated structure; forming droplets of the mixture in the channel via an in-channel three-valve elastomeric pump, wherein the pumping frequency and the droplet formation frequency have a 1:1 correspondence; routing the droplets to a nozzle to form a plurality of monodisperse emulsion droplet, at least some of which encapsulate PCR reagent, a single primer-functionalized microbead and a single target molecule or cell; and thermally cycling the droplets encapsulating PCR reagent, a single primer-functionalized microbead and a single target molecule or cell to produce a plurality of beads having amplicon of the target attached thereto.

Another aspect of the invention relates to a high-throughput method of screening a cell population, providing a reagent and cell mixture to a reagent inlet channel on a microfabricated structure; forming picoliter or nanoliter-volume droplets of the mixture in the channel via an in-channel three-valve elastomeric pump, wherein the pumping frequency and the droplet formation frequency have a 1:1 correspondence; routing the droplets to a nozzle to form a plurality of monodisperse emulsion droplets encapsulating reagent and a single cell, sorting the emulsion droplets to detect which droplets contain a cell; and analyzing each droplet containing a cell.

BRIEF DESCRIPTION OF DRAWINGS

The invention may best be understood by reference to the following description taken in conjunction with the accompanying drawings that illustrate specific embodiments of the present invention.

FIGS. 1A and 1B are diagrammatic representations of a process of producing nanoliter emulsion particles in accordance with embodiments of the invention.

FIG. 3E shows an optical micrograph of droplet generation at a cross-injector of a µDG.

FIG. 3F shows an optical micrograph of the droplets collected from the µDG having a predicted stochastic distribution of beads.

DETAILED DESCRIPTION

Figures 2A, 2B:
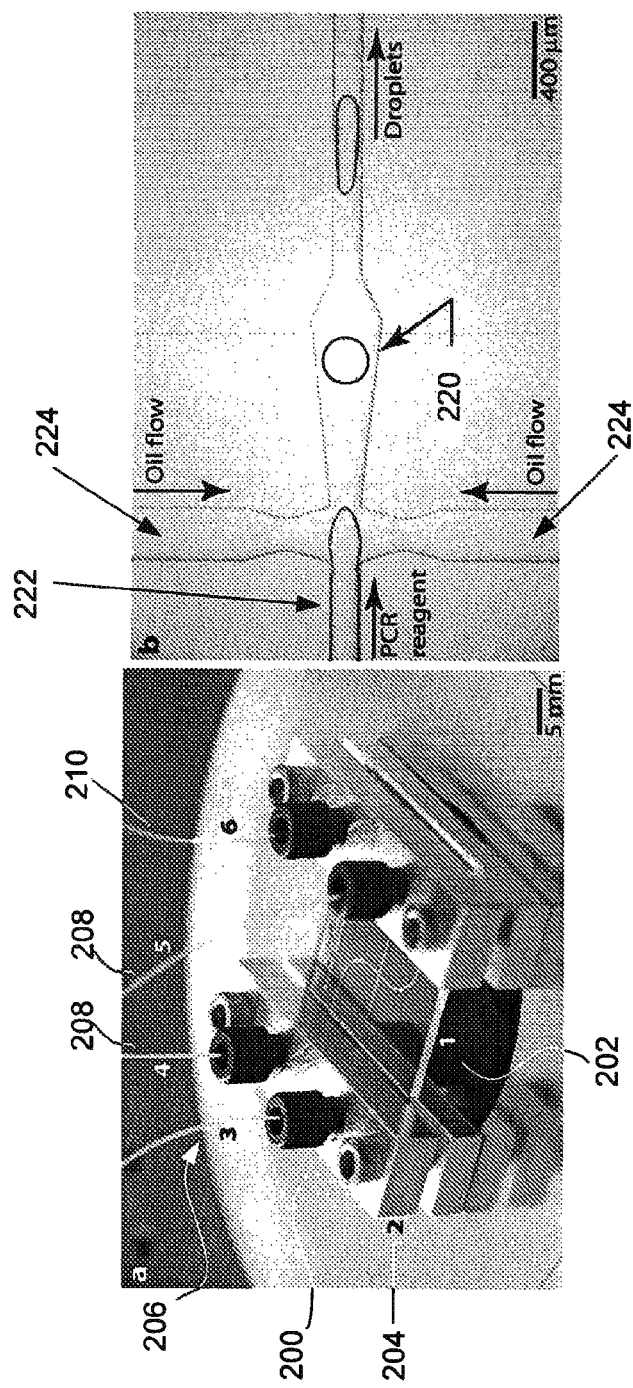
FIG. 2A is a photographic representation of a microfabricated emulsion generator device that may be used in accordance with embodiments of the invention.
FIG. 2B is an optical micrograph of droplet generation at the nozzle.

Reference will now be made in detail to some specific embodiments of the present invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. The present invention may be practiced without some or all of these specific details. In other instances, well known process operations have not been described in detail in order not to unnecessarily obscure the present invention.

Microemulsion droplets as reactor vessels have the potential for widespread application. For example, next generation DNA-sequencing techniques eliminate cloning-based DNA library preparation by using one-step in vitro amplification of sheared genomic fragments using microemulsion technology. However, current emulsion droplet methods lead to non-uniform amplification and are limited to short DNA amplicons (about 250 bp) due to the small and variable volume of the emulsions. Using conventional methods, polydisperse droplets (volume ranging from 1-100 pL) are generated.

The devices and methods described herein provide uniform and controlled picoliter or nanoliter-volume droplets (e.g., droplet size varying no more than a few percent), controlled generation frequency, and effective target incorporation.

In certain embodiments, these microemulsion droplets are used for efficiently performing PCR amplification of small amounts of template in a massively parallel format. This approach is valuable because: (1) the template and its PCR progeny are contained in a small nanoliter (nL) volume emulsion particle, enabling efficient amplification to produce a PCR colony contained in the bolus and chemically linked to a bead; (2) the isolated emulsion particles reduce contamination and false amplification by separating the various amplification reactions; (3) the comparatively high concentration of a single template target in these nL bolus enables efficient single molecule/single target amplification; and (4) the use of emulsion particles enables the massively parallel PCR amplification and analysis of large numbers of targets. PCR amplification is just one example of an application the microdroplet generator described herein may be used for. Massively parallel reactions of involving any single target molecule/cell in each reactor are possible using the microdroplet generator.

FIGS. 1A and 1B present a schematic of a method of producing nanoliter emulsion particles according to one embodiment, in which nanoliter-sized droplets containing PCR reagent, a target molecule and a reverse primer attached bead are formed. Target DNA or cells and beads are mixed with PCR reagent at very dilute concentrations and pumped through a microdroplet generator (µDG). Dilutions of both beads and target molecules allow encapsulation of a primer-functionalized bead and the target in individual droplets; a single target DNA molecule or cell is encapsulated in an individual reaction droplet by introducing it in very dilute concentrations in the PCR (or other) reagent. The reagent and target molecules approach a cross-injector 104 from the left side of a channel 102; carrier oil is flowed toward the cross-injector 104 from the two oil channels 107. Monodisperse nanoliter volume droplets of the PCT reagent are formed in a carrier oil at the cross-injector 104. The number of droplets containing a single bead and a single target DNA/cell is controlled by varying their concentrations in the PCR solution and by controlling droplet volume. For example, PCR reagent, target molecules and reverse primer attached beads (in channel 102) mixed at a dilution level sufficient to generate 1% of the droplets produced at the cross-injector 104 having both a cell and a bead functionalized with reverse primer. The µDG rapidly forms uniform volume reaction droplets in an immiscible carrier oil at the cross-injector 104. Droplet size is tunable; e.g., from about 100 pL to about 10 nL, in a particular example, between about 2-5 nL and uniform within a few percent, e.g., having variation of no more than about 2% from droplet to droplet. A droplet with both a cell and bead is shown at 106. Thousands of such droplets, generated at the cross-injector 104 within minutes, are collected in a standard reaction tube 108 and temperature cycled (or otherwise reacted) in parallel for high throughput.

FIG. 1B shows contents of a single droplet at 109, including the reverse primer attached bead, target (cell/DNA fragment) and dye labeled forward primers. Amplification in the droplet produces a large number of double stranded products that are linked to the bead by the covalent reverse primer. This is illustrated at 110. Dye labeled forward primers in solution allow for fluorescence detection of beads populated with the amplified target molecule. A bead with a large number of fluorescently labeled double stranded products is shown at 112.

FIG. 2A is a photographic representation of a microfabricated nozzle device 200 according to certain embodiments that rapidly generates controlled, nanoliter volume droplets of PCR reagent in oil and routes them into a 0.6 mL tube for temperature cycling using a block thermal cycler. The microdevice includes oil and aqueous fluidic interconnections, along with the droplet outlet tubing. A microfabricated chip 202, a fluid interconnect 204, a PCR mix inlet microtube 206, oil inlet microtubes 208 and a PCR droplet outlet 210 are indicated. Accurate infusion of oil and aqueous phases is enabled by the use of syringe pumps (PHD 2000, Harvard Apparatus) and glass syringes (Gastight syringe, Hamilton Company). Microtubing (Peek tubing, Upchurch Scientific) with about 100 µm internal diameter is used to minimize dead volume in the connections. FIG. 2B shows an optical micrograph of droplet generation at the cross-injector nozzle 220 of the device of FIG. 2A. PCR reagent is injected in the left channel 222, while oil is injected in the top and bottom channels 224. Droplet breakage at the nozzle occurs as a result of competition between viscous stresses associated with the imposed flow field and capillary stresses due to surface tension between the two phases. Further, surface modification with octadecyltrichlorosilane renders the channel walls, which may be glass and hydrophobic, thereby aiding in droplet formation and preventing any droplet-wall interaction downstream. This is important for preventing cross-contamination between droplets. The oil-surfactant combination used for emulsion generation is also important from two standpoints. First, it should allow droplet formation and maintain droplet stability through temperature cycling. Second, it should be compatible with single molecule analysis by minimizing enzyme/DNA adsorption to the active oil-aqueous interface. Various oil-surfactant combinations have been explored for microfabricated emulsion generation and show stable droplet formation but exhibit a high degree of enzyme adsorption. Two oil-surfactant formulations: (1) Mineral oil, 4.5% (v/v) Span 80, 0.4% (v/v) Tween 80 and 0.05% (v/v) Triton X-100 (all Sigma) (Ghadessy, et al., *Directed evolution of polymerase function by compartmentalized self-replication*. Proc. Natl. Acad. Sci. U.S.A. 2001, 98, 4552-4557; Dressman et al., *Transforming single DNA molecules into fluorescent magnetic particles for detection and enumeration of genetic variations*. Proc. Natl. Acad. Sci. U.S.A. 2003, 100, (15), 8817-8822, incorporated by reference herein) and (2) 40% (w/w) DC 5225C Formulation Aid (Dow Chemical Co., Midland, Mich.), 30% (w/w) DC 749 Fluid (Dow Chemical Co.), and 30% (w/w) Ar20 Silicone Oil (Sigma) (Margulies et al. *Genome sequencing in microfabricated high-density picolitre reactors*. Nature 437, 376-380 (2005)) have been successfully used for single molecule DNA amplification/analysis in a conventional polydispersed emulsion PCR format.

The oil formulation presented by Margulies et al., referenced above, was used to show stable droplet formation as well as successful amplification from a single DNA molecule in uniform volume nanoliter droplets. Reaction volumes of about 1-5 nL were used, as they contain more than 10 fold excess reagent for efficient amplification of >1000 bp amplicons and at the same time are small enough to keep the effective concentration of the single DNA molecule high (0.5-1.5 fM). Control over droplet size and generation frequency is achieved by (1) controlling the channel dimensions at the nozzle and (2) by varying the relative flow rates of oil and PCR reagent. Standard glass microfabrication may be used to etch the nozzle shown in FIG. 2B to a depth of 65 µm. Access holes (500 µm diameter) are drilled and enclosed channels are formed by thermally bonding the patterned glass chip with another glass slide. Using this device, three different droplet sizes—1.1 nL, 2.2 nL and 4.0 nL—may be generated by varying the total oil flow rate between 4.0, 2.0 and 1.0 µL/min, respectively, while keeping the PCR reagent flow rate constant at 0.5 µL/min. All the droplet sizes show stability after 40 cycles of PCR.

To validate the usefulness of the µDG for single molecule genetic analysis, a 1,008 bp region of the pUC18 genome was amplified from three different template dilutions in 2.2 nL droplets. Following PCR, droplets were purified to remove the oil phase and the extracted amplicons were run on an agarose gel. Gel quantitation showed three to five attomoles of product per template molecule consistently generated for the three different starting average template concentrations of 0.67, 0.067 and 0.0067 molecules/droplet. In particular, clear production in the lanes showing PCR amplified product produced from 1600 and 3200 droplets with corresponding concentrations of 0.067 and 0.0067 strands per droplet, respectively, demonstrates that full length 1 kb amplicons appropriate for sequencing can be produced from single template molecules in individual emulsion bolus. However, the PCR yields were about 20 fold lower than required by an attomole-scale inline-injection sequencing device. Two reasons for this low yield are (1) DNA template and enzyme adsorption to the glass syringe wall and (2) enzyme adsorption to the oil-aqueous interface in the high surface area to volume ratio droplets. The syringe can be coated with PEG-silane, poly-N-hydroxyethylacrylamide (pHEA) or with (poly)dimethylacrylamide, all of which have been shown to minimize DNA/enzyme adsorption to glass. To minimize enzyme adsorption to the oil-aqueous interface, surfactants such as Tween 80 or Triton X-100 can be included in the PCR mix. Alternatively, the oil-surfactant formulation presented by Ghadessy et al. and used by Dressman et al., both referenced above, or other appropriate formulations for single DNA molecule amplification, may be used.

In order to manipulate products amplified from distinct DNA templates/cells in individual droplets, primer functionalized microbeads may be incorporated in the droplets so that they are bound to the PCR progeny. Primer functionalized microbeads are mixed with PCR reagent and introduced into droplets along with a single DNA molecule/cell at ratios that follow the Poisson distribution. See Margulies and Dressman, both referenced above, for a demonstration of this in conventional polydisperse emulsion PCR formats. This capability with the µDG is extremely useful because of the added advantages of efficient, uniform and large (>1 Kb) product amplification on beads. In certain cases, flowing 22-44 µm diameter 6% agarose beads in droplets along with PCR reagent from a syringe into the device shown as in FIG. 2A, results in beads settling in the syringe as well as the chip input hole over time and not getting uniformly incorporated in the droplets.

In certain embodiments, the µDG has on-chip elastomeric valve pumping that provides pulsatile flow. In certain embodiments, there is correspondence between droplet generation frequency and pump pulses; thus the pulsatile nature of the on-chip valve pumping provides precise control over droplet generation frequency. Droplet size and volume fraction may be exactly determined by varying controlled physical parameters such as the pump size, actuation pressure/vacuum and intervals. This control is crucial for generating droplets in an optimum volume range for thermostability, for keeping effective concentration of the single target molecule/cell high within the droplet (e.g., on the order of a fM for single copy DNA template), and to ensure the correct quantity of starting reagents.

Figures 3A, 3B:
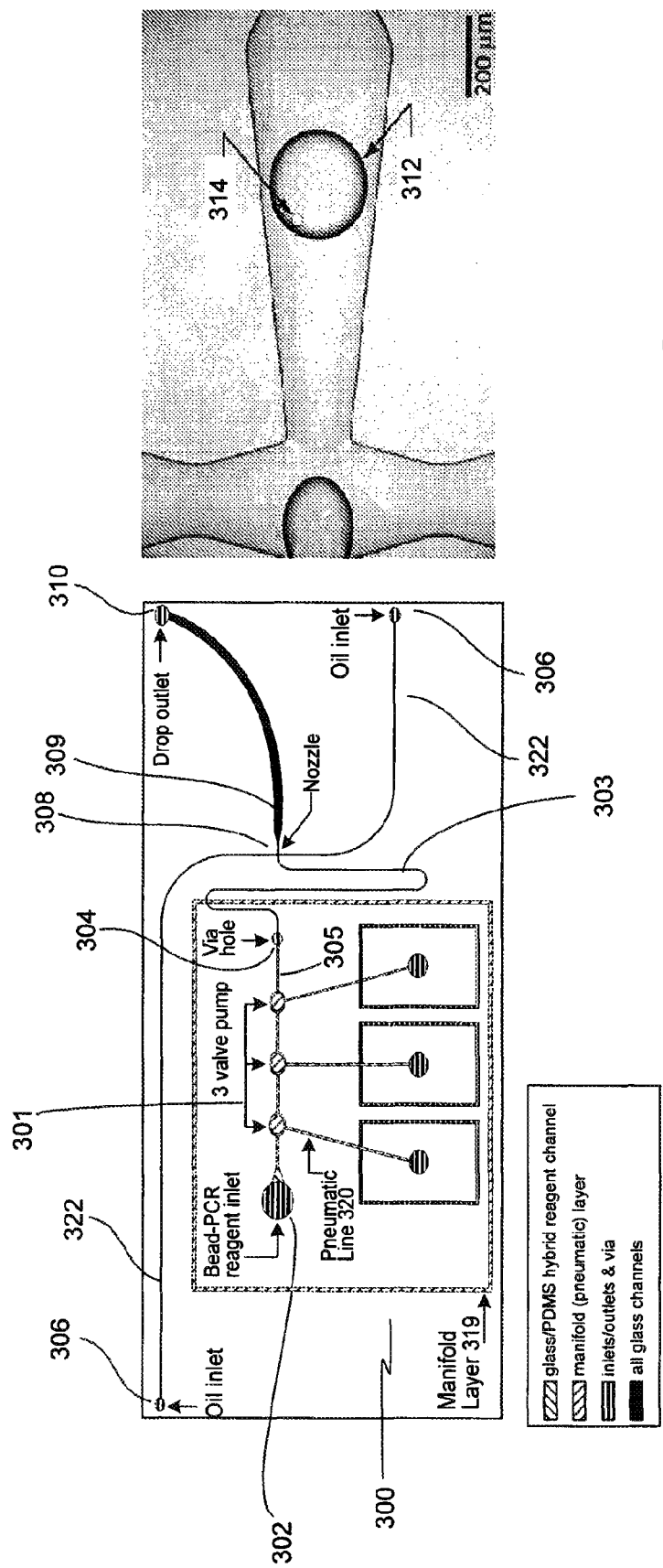
FIG. 3A is a diagrammatic representation of a microfabricated emulsion generator device layout that may be used in accordance with embodiments of the invention.
FIG. 3B is an optical micrograph of droplet formation at the nozzle. (A 34 µm diameter agarose bead is encapsulated in a 2.2 nL droplet.)

FIG. 3A shows a schematic of a µDG 300 with an on-chip pump 301 that has pulsatile flow that has been shown to facilitate bead movement in microchannels. The use of an on-chip pump for bead-PCR mix flow has two additional advantages: (1) it obviates the use of a syringe for PCR reagent and hence, negates the problem of DNA/enzyme adsorption to the syringe glass, and (2) the pulsatile motion provides active control over the droplet formation process. The bead-PCR mix is pipetted into a reservoir (not shown) placed over a bead-PCR reagent inlet hole 302 and withdrawn into the chip using the glass-PDMS-glass pump system described in Grover et al., *Monolithic membrane valves and diaphragm pumps for practical large-scale integration into microfluidic devices*. Sensors & Actuators B 2003, 89, 315-323, incorporated by reference herein. Oil is introduced directly into all-glass channels 322 at oil inlets 305 using syringe pumps (not shown). The PDMS swells on contact with oil so it is kept spatially separated from the oil. Droplets are generated at a nozzle 308 and routed out of the device at a droplet outlet 310 via all-glass channel 309.

The µDG 300 shown in FIG. 3A is a four-layer sandwich having a blank glass wafer, a microfabricated glass fluidic wafer, a featureless PDMS (or other elastomeric) membrane, and a microfabricated manifold wafer. The three layer (glass-PDMS-glass) pneumatically controlled micropump 301 is integrated on-chip to deliver reagent. The manifold layer, indicated at 319, controls valve actuation, and a via hole 304 connects the glass-PDMS hybrid channel 305 to the thermally bonded all-glass channel 303 and cross-injector 308. Reagent mix from the glass-PDMS channel 305 flows into the all-glass channel 303 through via hole 304. (Etch depth about 100 µm).

In certain embodiments, the enclosed all-glass channels (i.e., channels 322, 303 and 309), are formed by thermally bonding the blank wafer to the patterned side of the fluidic wafer. The diced bottom stack is contact bonded by the PDMS membrane to the manifold wafer forming the microvalves and a three-dimensional fluidic interconnect. (See, Grover, et al., *Monolithic membrane valves and diaphragm pumps for practical large-scale integration into microfluidic devices.* Sensors & Actuators B 2003, 89, 315-323, incorporated by reference herein). After fabrication, the cross-injector 308 is rendered hydrophobic, e.g., with octadecyltrichlorosilane (OTS) treatment, and fluidic connections between carrier oil filled syringes and the device can be made using microtubings, custom ferrules and custom aluminum manifolds. The terms cross-injector and nozzle are used interchangeably in the specification. Injectors used in the μDGs described herein are not limited to cross-injectors, but may be any type of injector configured to generate emulsion droplets, e.g., T-injectors, etc. For further description on injectors that may be used in accordance with the invention, see Song H, Tice J D, Ismagilov R F (2003) A microfluidic system for controlling reaction networks in time. Angew. Chem. —Int. Edit. 42: 768-772, incorporated by reference herein.

While FIG. 3A shows a schematic representation of a four-layer sandwich, in certain embodiments, a 3-layer sandwich is used, with the oil pumped directly intersecting with the glass-elastomer hybrid channel 305. In this case, via hole 304 is not necessary. The four-layer sandwich is appropriate for cases in which the oil and the elastomer are incompatible; for example, in certain situations PDMS tends to swell when in contact with oil.

Figure 4A:
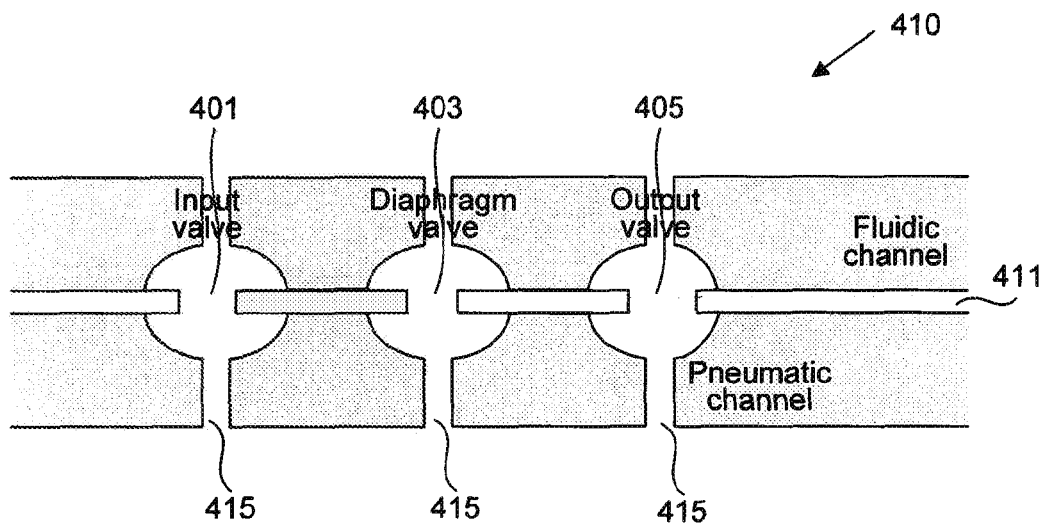
FIGS. 4A and 4B are diagrammatic representations depicting a three-valve diaphragm pump that may be used with implementations of the present invention.
Figure 4B:
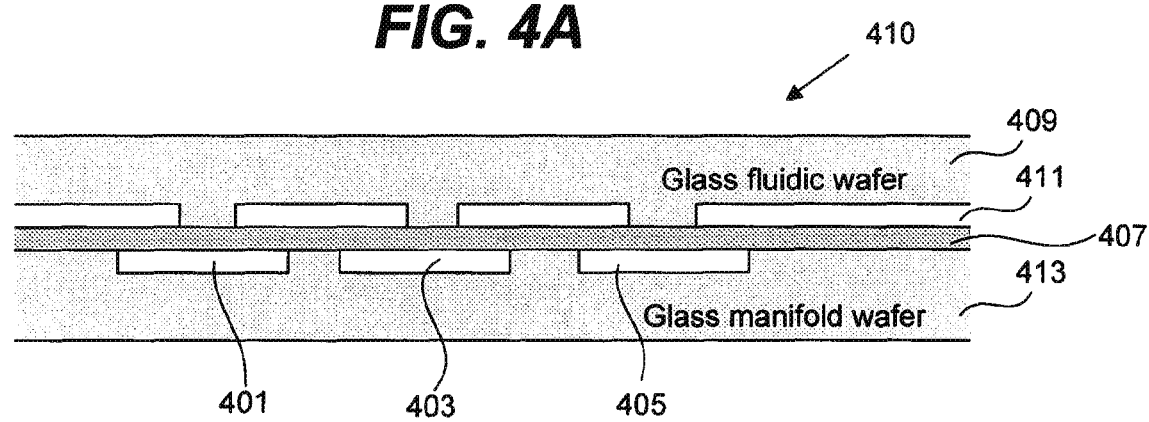

FIGS. 4A and 4B are diagrammatic representations of a three-valve pump 410 formed using membrane valves, with FIG. 4A showing a top view of a three-layer monolithic membrane diaphragm pump and FIG. 4B showing a side view of the three-layer monolithic membrane diaphragm pump. According to various embodiments, the various fluid control components within the monolithic membrane device are actuated by applying pressure or vacuum to holes on the pneumatic wafer. Any single membrane is referred to herein as a monolithic membrane. Any single device with a monolithic membrane is referred to herein as a monolithic device. The diaphragm pump includes an input valve 401, a diaphragm valve 403, and an output valve 405. Portions of fluidic layer 409 with etched fluidic channels 411, monolithic membrane 407, and a manifold layer 413 are shown in FIG. 4B. Manifold channels 415 are used to deliver pneumatic actuation to valves 401, 403 and 405. The three-valve pump is described in U.S. Patent Publication No. 20040209354, incorporated by reference herein.

Figure 4C:
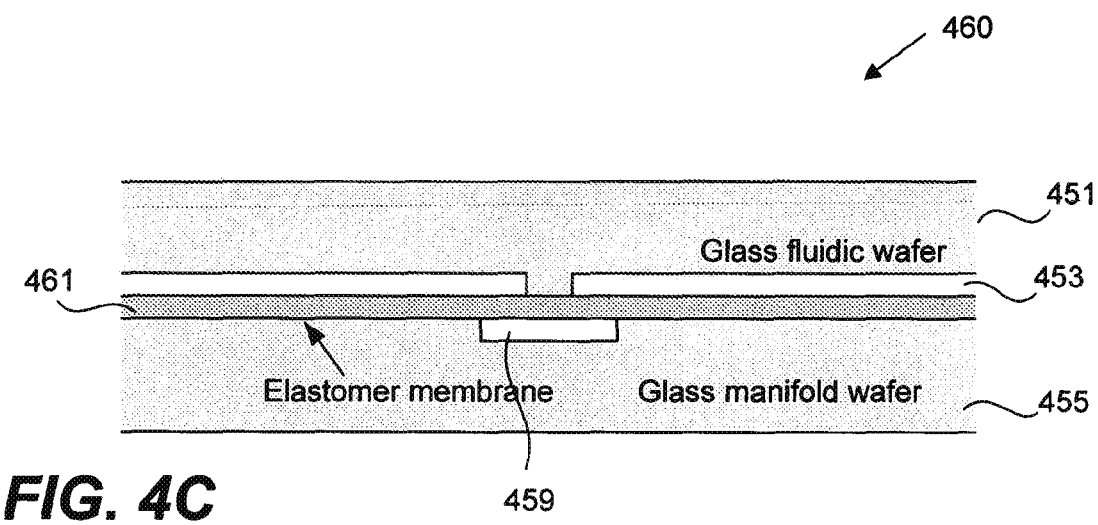
FIGS. 4C and 4D are diagrammatic representations showing, respectively, open and close diaphragm valves that may be used with implementations of the present invention.
Figure 4D:
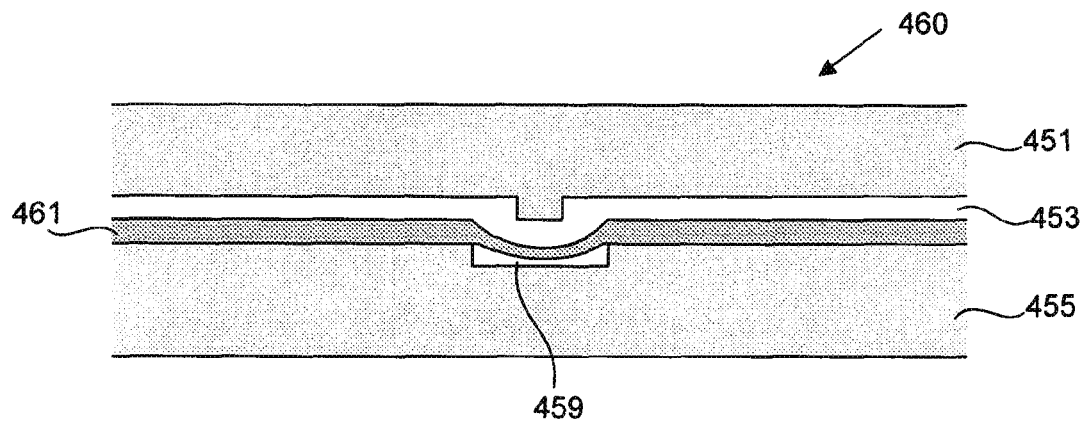

According to various embodiments, pumping can be performed in a series of stages by opening and closing the valves. FIGS. 4C and 4D illustrate an example of a valve 460 in a closed (FIG. 4C) and open (FIG. 4D) position. Etched channels associated with pneumatic wafer 455 distribute the actuation vacuum to valve region 459 of the elastomer membrane 461. Vacuum applied via the manifold channel (pneumatic channel 415 in FIG. 4A) at valve area region 459 deflects the membrane away from the channel discontinuity, providing a path for fluid flow across the discontinuity and thus opening the valve as shown in FIG. 4D. Valves that can be opened or closed using pneumatic pressure are herein referred to as switchable valves or pneumatically switchable valves. Applying pneumatic pressure includes either applying pressure or applying a vacuum. The membrane 461 consequently can modulate the flow of fluid in the adjacent fluid channel as shown in FIG. 4D. In FIG. 4D, a vacuum is applied to valve area 459 through etched channels associated with pneumatic wafer 455 to open fluidic channel 453. When vacuum pressure or suction is no longer applied to valve area 459, the membrane 461 closes the fluidic channel 453 as shown in FIG. 4C.

Returning to FIG. 4B, pumping can be performed in a series of stages. In a first stage, output valve 405 is closed and an input valve 401 is opened. In a second stage, the diaphragm valve 403 is opened. In a third stage, the input valve 401 is closed. In a fourth stage, the output valve 405 is opened. In a fifth stage, the diaphragm valve 403 is closed, pumping fluid through the open output valve 405. The volume pumped per cycle is determined by the volume contained within the open diaphragm valve, a volume that, in turn, determined by the size of the pneumatic chamber in the diaphragm valve. Therefore, pumps designed for metering known nanoliter scale volumes of fluid can be fabricated by modulating the size of the diaphragm valve pneumatic chamber.

Returning to FIG. 3A, in operation, pressure and vacuum signals are transferred by the pneumatic control lines 320 to the three microvalves that form the micropump 301. The microvalves pump reagent containing the target, and in certain embodiments, a microcarrier such as a bead, through the via hole 304 to the all-glass channel 303. A syringe pump is used to continuously infuse carrier oil into the all-glass channels 322 through inlet ports 306.

FIG. 3B presents an optical micrograph of an engineered 2.2 nL droplet 312 containing a 34 μm agarose microbead 314 formed with the μDG device shown in FIG. 3A. The pulsatile motion of on-chip pumping aids in droplet formation and provides a remarkable 1:1 correspondence between pumping frequency and droplet formation frequency. Hence the droplet volume is equal to the volume pumped every stroke, which in turn is proportional to the volume of the valves. This enables good control over droplet volumes by fabricating corresponding size valve pumps.

Figures 3C, 3D:
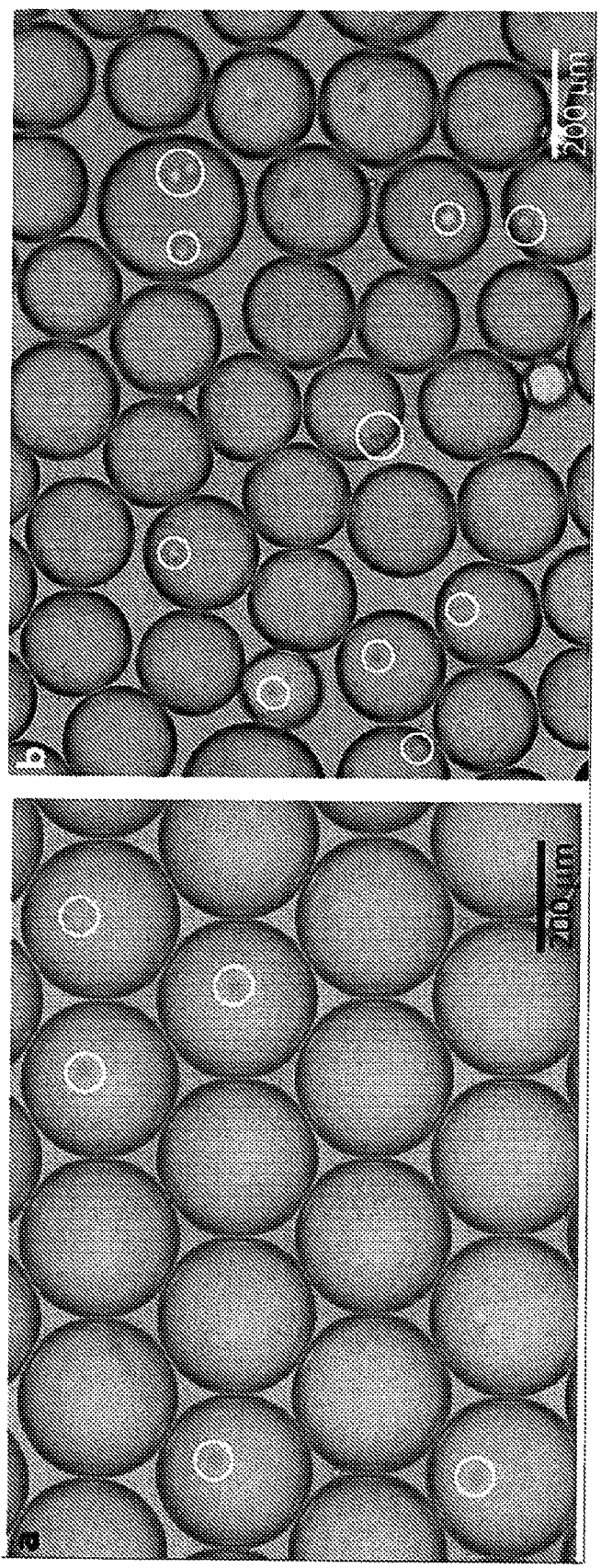
FIG. 3C shows highly uniform 13 nL droplets collected from a microdroplet generator according to an embodiment of the invention and imaged prior to thermal cycling. (Individual beads in five droplets are highlighted with circles around them.)
FIG. 3D shows 4 nL droplets with beads after 40 cycles of PCR, formed by operating the on-chip pump at 5.5 Hz and setting the combined oil flow rate to 6.0 µL/min.

FIG. 3C shows highly uniform 13 nL droplets collected from the μDG and imaged prior to thermal cycling that were formed with 1.0 mm×1.4 mm valves, etched to a depth of 100 μm. A pumping frequency of 3.3 Hz was used and the combined oil flow rate was set to 4.0 μL/min. Large droplets (5 nL and bigger) have reduced stability and merge on temperature cycling. FIG. 3D shows smaller (mean volume 4 nL) droplets (with beads) after 40 cycles of PCR that were formed by operating the on-chip pump at 5.5 Hz and setting the combined oil flow rate to 6.0 μL/min. Beads encapsulated by individual droplets are highlighted with circles around them. Running the on-chip as well as the syringe pump faster helps modulate the droplet size but may introduce some polydispersity. The μDG device may incorporate valves with volumes proportional to 100 pL-10 nL, e.g., between 2-4 nL, such that droplet uniformity can be attained in the smaller size range by running the on-chip and syringe pumps at moderate speeds. Alternatively, bigger valves may be used to prevent beads from being tapped in valves with bifurcation of the bead-PCR reagent channel, which addresses multiple nozzles. This allows the volumetric flow rate to be dropped by half or one fourth in each of the downstream channels and at the same time allows for parallel droplet generation at two or four nozzles with a single bead-PCR mix input.

In another example, droplets were generated at a frequency of 5.7 Hz with a combined oil flow rate of 2.2 μL/min and a PCR solution flow rate of 0.8 μL/min. The pumping region of the μDG was treated with a coating solution prior to droplet generation to minimize DNA/polymerase adsorption on the glass and PDMS surface. Following this, droplets were generated by infusing the carrier oil using a syringe pump and the PCR mix using the on-chip PDMS membrane pump. The on-chip pump operating at 5.7 Hz generated one 2.5 nL droplet every pumping cycle. Average bead concentration was 130 μL/min (0.33 bead/droplet). An optical micrograph of the droplet generation at the cross-injector is shown in FIG. 3E. FIG. 3F shows an optical micrograph of the droplets collected from the μDG having a predicted stochastic distribution of beads. (26% of droplets=1 bead). The droplets show a highly uniform diameter of 167+/−6 μm, corresponding to a volume of 2.4 nL with a variance of only 0.3 nL.

In certain embodiments, microbeads or other microcarrier elements are used to confine and manipulate the PCR or other product from each droplet. Linking the PCR progeny generated from a single DNA molecule or a single cell to primer functionalized microbeads (or other microcarrier elements) provides high throughput downstream manipulation or analysis.

Several types of beads have been successfully used as substrates for PCR, such as agarose beads, magnetic silica microbeads and polystyrene beads. All of these beads are commercially available with different size ranges. Agarose beads are the first choice because of their low density, hydrophilicity, minimal aggregation and high loading capacity. Magnetic silica microbeads allow simple and easy extraction of microbeads from the emulsion. However, the low loading capacity of silica microbeads beads (low attomole range) might prevent their use for a sequencing project, where 100 attomoles of 1 kb DNA product is desired on the bead surface. Being more uniform in size, polystyrene is a good choice for quantitation. A 9 μm polystyrene bead will have approximately 40 femtomoles of functional groups for surface conjugation. Overall, agarose beads have the highest number of functional groups per unit surface area. For example, agarose beads with a mean diameter of 34 μm have about 2 picomoles of functional groups for DNA coupling. Such a high loading capacity can ensure high PCR product yield on each bead.

Beads may be prepared in various manners. For example, N-hydroxysuccinimide ester (NHS)-activated agarose beads (34 μm mean diameter) (Amersham Biosciences) are washed with cold 0.1M HCl three times, cold $H_2O$ once, and cold 0.1M PBS (pH7.5) once to completely remove propanol in which the beads are stored. The beads and an amine labelled reverse primer are mixed in 0.1M PBS (pH7.5) and incubated overnight for coupling. The primer concentration in the reaction will be set to about 4000 attomole/bead. Typically, as high as 50% of coupling yield can be reached for the reaction between an amine and NHS ester in aqueous condition. It is expected that about 2000 attomoles of primer can be coupled to a single bead. As the number of NHS groups on each bead is about 2 picomoles, the number of primers attached to each bead can be easily increased when necessary by adding higher concentration of primer in the coupling reaction. After coupling, the beads are washed 3 times with 0.1M PBS to remove any unbound DNA and stored in pure water at 4° C. until needed. One potential problem of using the 34 μm agarose beads is their size polydispersity (ranging from 22-44 μm), which might result in significant variation in the number of DNA molecules generated on each bead even under controlled reaction conditions. This might not be a problem for sequencing and other qualitative applications. However, it could be a problem for quantitation. If this is found to be a problem, the size range of the beads may be narrowed by filtration methods.

To achieve optimum amplification yield and avoid the steric hindrance the solid surface (beads) poses to the polymerase in both PCR and sequencing reactions, the reverse primer may be conjugated to the beads via a polyethylene glycol linker. The length of polyethylene glycol (PEG) or the poly-T can be optimized to achieve the highest PCR yield and longest sequencing read length. Optimization of the following PCR parameters may be performed: forward primer concentration in solution, reverse primer density on beads, polymerase concentration, annealing time and extension time. Flow Cytometry (FACS) analysis of the DNA yield on each bead may be used to evaluate and optimize PCR conditions. The optimization experiments may be first carried out in solution without a microemulsion. Gel analysis of PCR production in solution may be performed to make sure no non-specific amplification occurs due to the altered PCR conditions. Recognizing the polymerase activity might decrease due to possible minor nonspecific adsorption of the enzyme to the oil-water interface, an optimization of PCR conditions in the droplet may also be performed with a focus on exploring the use of a surfactant, BSA or other additives to maintain optimum bead PCR efficiency.

The bead recovery process should remove oil and surfactants present in the emulsion completely so that they will not affect the downstream processing such as sequencing, genotyping, or quantitation of the DNA product on beads, with minimum loss of the secondary DNA strand that is hybridized to the bead bound strand. In certain embodiments, isopropyl alcohol is first used to dissolve the oil and surfactants. The solution is then passed through a 15 μm filter. The beads retained on the filter are washed three times with isopropyl alcohol, once with 100% ethanol and three times with 1×PCR buffer containing 1.5 mM $MgCl_2$. Results indicate that more than 70% of the beads can be recovered with about 90% of the DNA remaining double stranded.

Figures 5A, 5B:
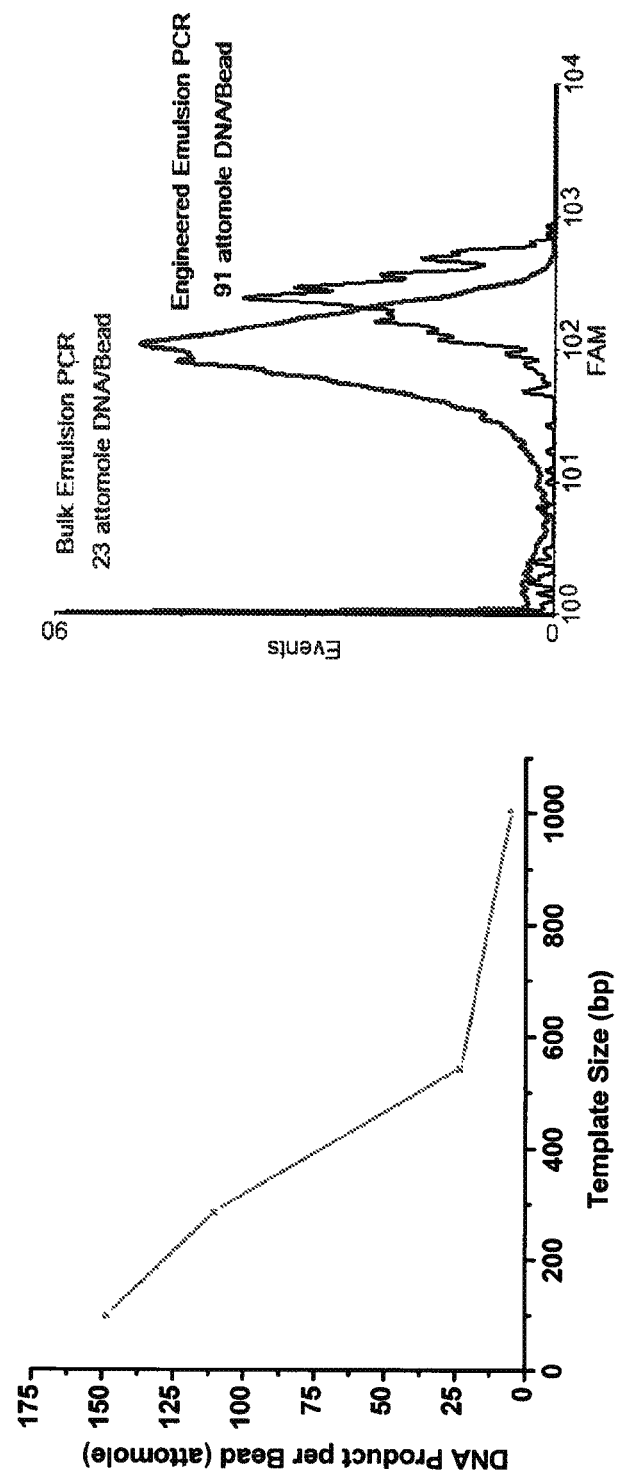
FIG. 5A shows a plot of the amount of DNA per bead generated using a bulk emulsion tissue lyser method with different template sizes.
FIG. 5B shows a plot comparing bead PCR yields from traditional emulsion PCR and the engineered emulsion PCR according to an embodiment described herein with a template size of 545 bp.

Bead PCR efficiency in microemulsions that were generated with a traditional tissue lyser method and the effect of amplicon size on bead PCR efficiency was studied. The tissue lyser approach produced very small (about 50 pL) emulsion droplets with a wide range of droplet sizes. Starting with 10 templates per bead, as high as 150 attomoles of 108 bp amplicon can be generated on each bead after 40 cycles of PCR. However, limited by the small volume of the droplets, the yield for long templates dropped significantly as shown in FIGS. 5A and 5B. FIG. 5A shows a plot of the amount of DNA per bead generated using the bulk emulsion tissue lyser method with different template sizes. FIG. 5B shows a comparison of bead PCR yields from traditional emulsion PCR and the engineered emulsion PCR according to an embodiment described herein with a template size of 545 bp. This result illustrates an important fundamental limit of the current conventional bulk emulsion PCR techniques. About 23 attomoles of DNA product was found when the template length was increased to 545 bp. Performing PCR under the same conditions with 4 nL-droplets generated with a μDG produced about 91 attomoles of 545 bp DNA product on each bead. These results establish that the bead PCR can be carried out in engineered emulsion droplets and that the droplets produced with the μDG device allow the amplification of long targets with high yield.

Figure 6A:
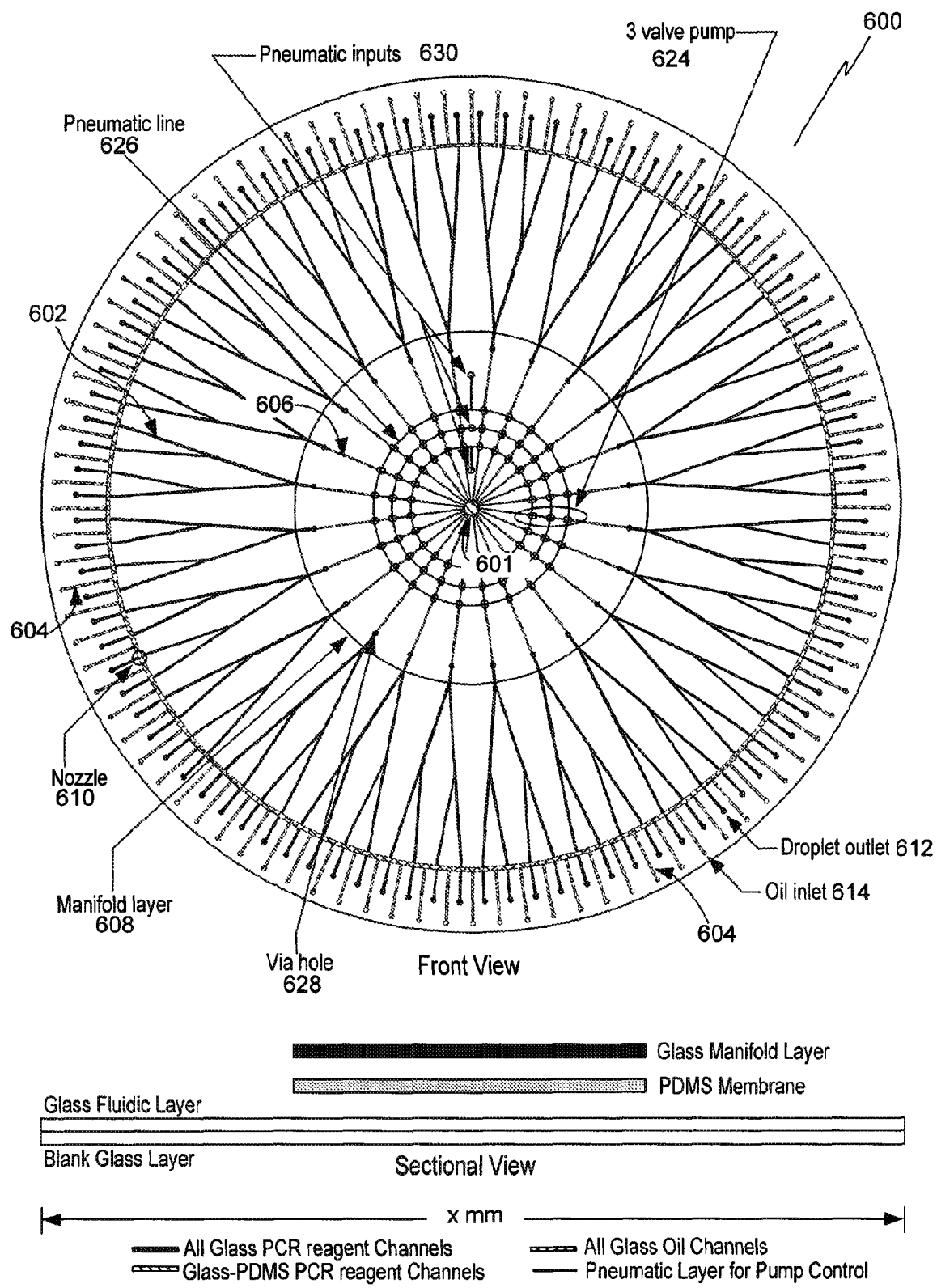
FIG. 6A is a diagrammatic representation of a 96 nozzle, high-throughput engineered microdroplet emulsion generator with a single reagent inlet hole at the center.
Figure 6B:
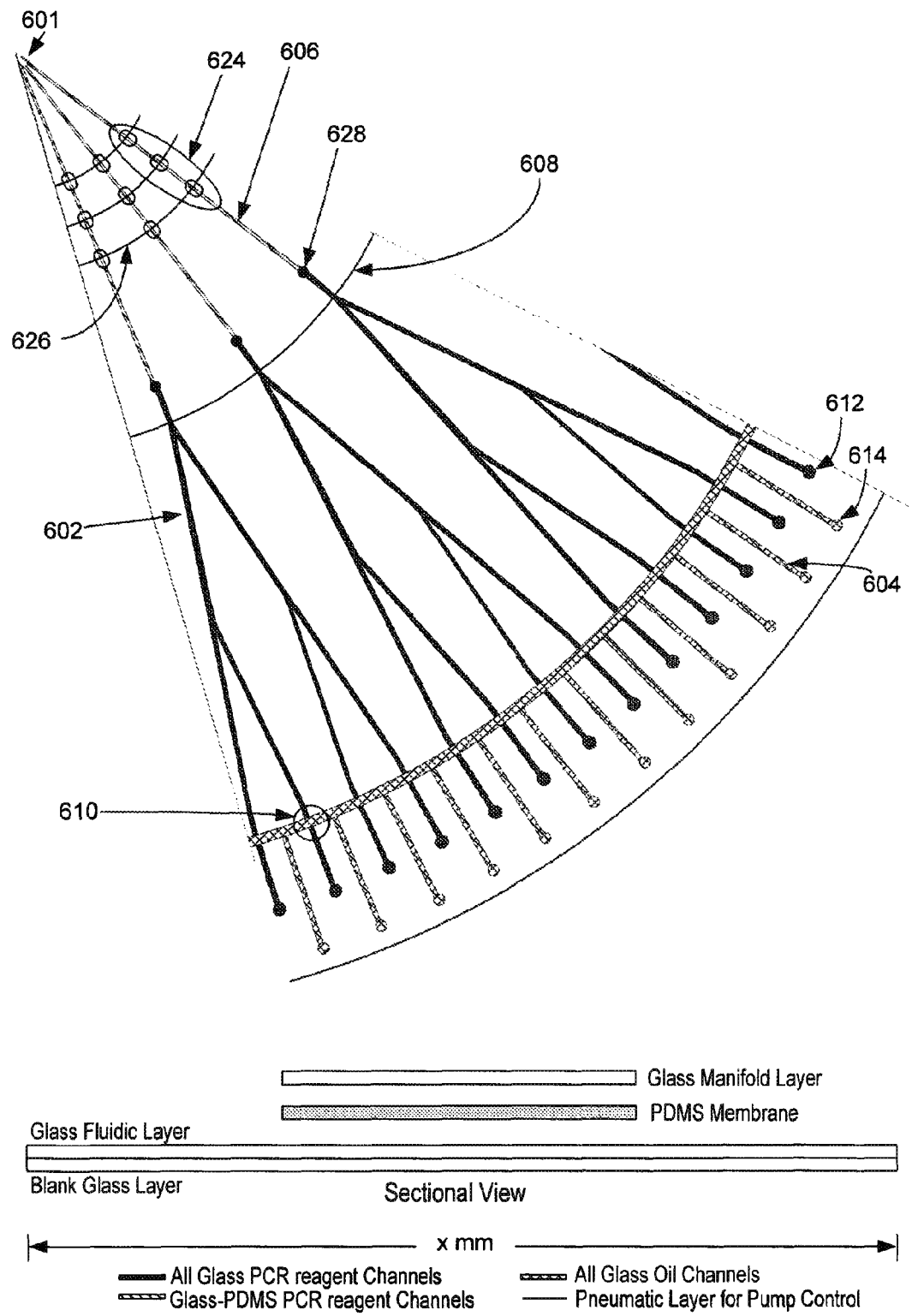
FIG. 6B shows an enlarged pie-section of the microdroplet emulsion generator shown in FIG. 6A.

FIG. 6A is diagrammatic representation of a polar arrayed μDG 600 with 96 nozzles that are all supplied by a single bead-PCR reagent inlet 601 at the center. (FIG. 6B shows an enlarged pie-section of the μDG 600). Diameter of the embodiment depicted in FIG. 6A is about 150 mm. Arrayed μDGs may be used for whole genome sequencing template preparation and other applications that require large numbers of nanoliter volume droplets. PCR reagent channels 602, glass-PDMS PCR reagent channels 606, and all glass oil channels 604 are indicated. PCR droplet outlets are shown at 612 and oil inlets at 614. A via hole 628 connects glass-PDMS channels to the all-glass channels. A pneumatic layer for pump control is indicated at 608. Twenty-four 3-valve on-chip pumps (valves are indicated at 624) are simultaneously controlled by three concentric pneumatic lines, indicated at 626, to infuse reagent through bifurcating channels into 96 nozzles 610. Each of the nozzles 610 is designed as the single nozzle 308 in FIG. 3A. Ninety-six oil inlet holes 614, each addressing two oil channels, each allow symmetrical oil flow and uniform droplet formation at the nozzles. The operation of the 24 on-chip pumping devices which, in turn, each address 4 nozzles through channel bifurcation is similar to the device shown in FIG. 3A. The polar array format limits the bead-PCR mix inlet to one hole 601 at the center but also combines the pneumatic control for the 24 pumps into just three pneumatic lines. Ninety-six oil input holes 614 allows oil phase flow into each of the two adjacent nozzles, thereby aiding in symmetrical and focused droplet release.

In operation, a mixture including PCR reagent, beads and targets is introduced to the device via inlet 601. Oil is introduced to the device via oil inlets 614. The reagent mixture flows from the inlet 601 in glass-PDMS hybrid channels 606 to pumps 624. The pumps are controlled by three concentric pneumatic lines 626, with each line 626 controlling one of the valves of each three valve pump 624. Three pneumatic inputs 630 are used to send vacuum/pressure pulses to the lines to simultaneously control the valves. The pumps 624 form monodisperse pulsatile flow of the reagent mix, with each pulse having a volume of 100 pL-10 nL, as desired. The pulsatile flow of reagent and target mixture flows outward radially along glass-PDMS channels 606 until it reaches vias 628, which connect the glass-PDMS channels to the all-glass reagent channels 602. These channels bifurcate, as shown in FIG. 6A. The reagent mix then intersects with oil channels 604 at nozzles 610, forming monodisperse emulsion droplets encapsulating the targets, reagent, and beads (if present). The droplets exit the device at outlets 612.

All the oil input and droplet output connections may be made through a circular custom interconnect, similar to that shown in FIG. 2A. Five infuse/withdraw syringe pumps (not shown) (Model#702006, Harvard Apparatus) with ten 1 mL gastight syringe holders each and a flow splitting connection (Upchurch Scientific) for all the syringes (1700 series, Hamilton Company) allow simultaneous and continuous addressing of the 96 oil lines. Alternatively, oil flow can be split into multiple lines within the microfabricated device, thus reducing the number of syringe pumps required. In the arrayed μDG, as all the on-chip pumps are simultaneously addressed by the three pneumatic lines, in certain embodiments, about 10-11 droplets/sec are generated at each of the 96 nozzles, enabling production of 1000 nanoliter volume droplets per second per wafer.

While aspects of the invention have been described above in the context of PCR, the μDG may be used to encapsulate any target molecule in monodisperse droplets, enabling high throughput massively parallel operations involving the target molecule. The μDG may be advantageously used for any operation that amplifies or sense a target molecule. In certain embodiments, the μDG formulates droplets that contain only single target molecule/cell. The amount of reagent in each droplet is highly uniform across all droplets, meaning that the amount of signal generated is highly correlated to the identity or concentration of the initial target. Because the μDG allows high throughput single cell analysis, it is possible to detect the presence of a bacterial cell that occurs at low frequency, e.g., 1 in 1,000, 1 in 10,000, 1 in 100,000 or lower. Unlike with bulk assays, in which signals at these rates would be lost in the noise, the single cell analyses methods described herein allow detection of such cells regardless of the frequency of occurrence. The μDG thus allows digital analysis of genetic and cellular signals. The level of gene expression, genetic variation, genetic identify can be found on a cell-by-cell basis for thousands or millions of cells in a high throughput assay. Also in certain embodiments, thousands or millions of experiments may be performed in parallel by using the in vitro compartmentalization of the μDG by appropriately selecting the target molecules or cells and reagents, without risk of cross-contamination by the parallel reactions. Because the volume of droplets produced by the μDG is uniform, the signal produced across the droplets are directly comparable. Any desired volume, between about 100 pL and 10 nL, is obtainable, precise to 1-2%. Current methods of droplet generation produce droplets varying in size as much as 50% or higher.

Examples of applications of the μDG according to various embodiments are presented below.

Amplification of a Genomic Library

An entire mammalian genomic library can be amplified at 6× coverage by a continuous, parallel run of three array μDGs (as shown in FIG. 6A) in less than or about 48 hours. For a human genomic library consisting of 1000 bp fragments ligated into a plasmid (TOPO Shotgun Subcloning Kit #K7000-01)—thereby, enabling universal priming—this implies amplifying 18 million ((3 billion bp/1000 bp fragments)×6) plasmid DNA templates. By using dilutions of both the bead and plasmid, a single bead and template molecule can be isolated within a PCR droplet with a frequency predicted by the Poisson distribution. Plasmid dilution corresponding to an average of 0.1 molecule/2 nL droplet (0.8 fM) and bead dilution corresponding to an average of 1.0 bead/2 nL droplet ($5 \times 10^5$ beads/mL) will give 3.33% (Probability$_{single\ plasmid}$×Probability$_{single\ bead}$) droplets generating clonal beads. Therefore, the total number of droplets to be generated is about 540 million (18 million/0.0333). This number of droplets can be generated in about 48 hours with a parallel operation of three array μDGs shown in FIG. 6A (540 million/(3000 Hz×3600)). In one example, the clonal beads are sorted from the beads with no DNA using a BD FACSArray (BD Biosciences) flow cytometer with a processing speed of up to 15,000 events per second. When the forward primer is not labelled, the beads that are destined for sequencing will be treated with an intercalation dye such as TO that is not fluorescent until intercalated into ds-DNA. The fluorescence intensity of TO is linearly proportional to the amount of DNA, allowing differentiation between beads that have amplified DNA and those that do not. The percentage of non-clonal beads that are generated is dictated by the probability of two or more plasmids in a single droplet relative to all productive droplets and is <5% for a concentration of 0.1 DNA molecule/2 nL droplet. These beads can be differentiated at the sorting step based on their expected higher fluorescence yield. Alternatively data from nonclonal beads can be discarded based on their (unreadable) sequence at the sequencing step. The μDG device can meet the large clonal template amplification requirements of future generation whole genome Sanger and Pyrosequencing platforms.

Screening of Single Pathogenic Bacterial/Cancer Cells in a Background of Commensal/Wild Type Cells The high-throughput array μDG 600 can also be used for rapid screening of single pathogenic bacterial/cancer cells in a background of commensal/wild type cells. For detecting one such occurrence amongst 10,000 commensal/wild type cells, about 10,000 cells are encapsulated in individual bead-containing droplets. Incidence of single cell and single bead in a droplet can again be predicted by Poisson distribution for dilutions of both cells and beads. Using cell dilution corresponding to an average of 0.1 cell/2 nL droplet ($5 \times 10^4$ cells/mL) and bead dilution corresponding to an average of 0.1 bead/2 nL droplet (5×10⁴ beads/mL), one cell and one bead are obtained in 0.82% (Probability$_{single\ cell}$×Probability$_{single\ bead}$) of droplets. A total of ~1.2 million (10,000/ 0.0082) droplets are needed to be generated to analyze a pool of 10,000 cells using the μDG. This can be achieved by a single array μDG running at 1000 Hz in 20 minutes (1.2 million/(1000 Hz×60)). The μDG can, hence, effectively be used in rapid diagnostic and screening applications involving detection of rare cell types in a background of more common cell lines.

Analysis of Bacterial Cells

Also provided are methods of using μDG technology for high throughput single cell analysis. In certain embodiments, the methods involve incorporating a single cell and a single bead in single emulsion droplets, performing single cell PCR in emulsion droplets, and interrogating the genomic information of each individual cell through analysis, e.g., FACS analysis, of the genetic products produced on the bead. For example, a pathogenic bacteria such as *E. coli* O157 in *Escherichia coli* K-12 cells may be detected.

In certain embodiments, the methods involve diluting cells, e.g., *E coli* K12 cells and beads labelled with reverse primer specific for the desired targets in the cells in a PCR reaction mixture and flowing the mixture into a μDG to form emulsion droplets. For example, both the cell solution and the bead solution are diluted to such an extent that on average only one in ten droplets contains a cell and one in ten droplets contains a bead. The inclusion of beads and cells in a droplet is a random process and is determined by Poisson statistics. Under the diluted condition, the majority (>90%) of droplets that have both beads and cells will contain only one cell and one bead. Statistical analysis also predicts that only about one percent of the droplets generated will contain both a cell and a bead. By generating 100,000 droplets, about 1000 cells can be analyzed, which is sufficient for a statistically meaningful single cell analysis. At a 10 Hz droplet generation frequency, it will take a single droplet generator two and a half hours to prepare these droplets. Using a wafer that has an array of 96 the time will be reduced to less than 2 minutes.

In certain embodiments, the cell suspensions are monitored by microscopy to ensure single cell dispersion and sonicated briefly to disperse. Also in certain embodiments, a polymerase, such as AmpliTaq Gold polymerase, that requires a 10 minutes activation step may be used to ensure that cell lysis is successful. In addition, low concentrations of surfactants could also be used to facilitate cell disruption. Inhibition of PCR, e.g. by the *E. coli*, may be addressed by increasing polymerase concentration, by adding BSA as a carrier, and by using different polymerases.

Figure 7:
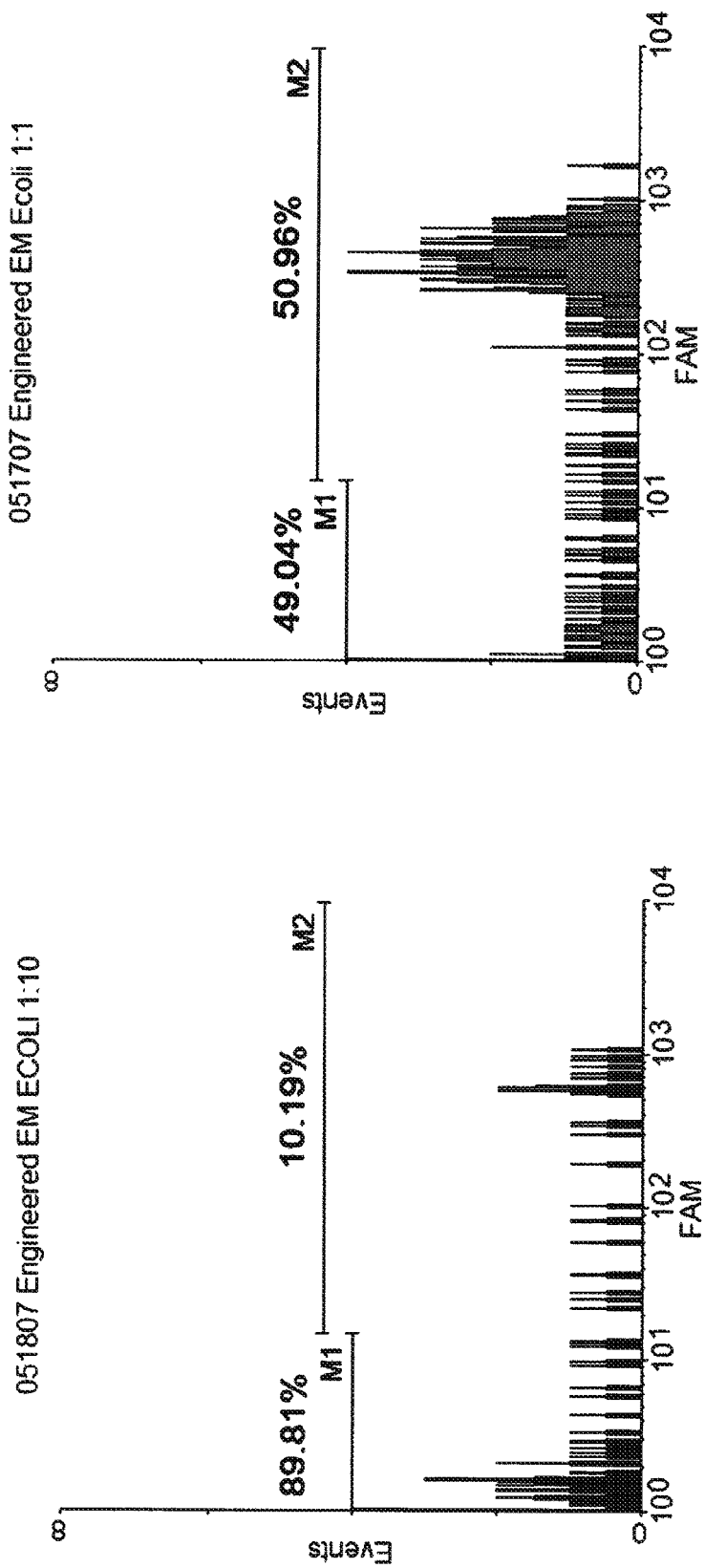
FIG. 7 shows results of analyzing single *E. coli* K12 cells in engineered droplets according to certain embodiments of the invention.

FIG. 7 shows results of analyzing single *E. coli* K12 cells in engineered droplets in Agarose beads that were conjugated with reverse primer (NH$_2$-PEG-CACTTTCACG-GAAACGA CCGCAAT) targeting the gyr B gene of *E. coli*. The mean concentration of agarose beads was about 0.15 beads per droplet. The forward primer was FAM labeled (FAM-TTACCAACAACATTCCGCA GCGTG). Bacteria were diluted to about 0.1 and 1 cell per droplet. 18,000 droplets were generated by the μDG and collected in three PCR tubes. After 40 cycles of PCR, the beads were extracted and analyzed by FACS. As indicated in FIG. 7, the beads exhibited a bimodal distribution as expected. One set of beads had no/low fluorescence, while the other set was highly fluorescent. The percentage of the beads in each population matched with statistical calculations. For example, with a cell concentration of 0.1 per 1 droplet, the probability of having droplets with at least one cell is about 0.095 ($p=1-e^{-0.1}*(-0.1)^0/0!$). Any beads delivered into a droplet will have a probability of 0.095 to meet with at least one cell and thus get amplified and modified with FAM labeled DNA product. FACS analysis showed that the percentage of the beads in the brighter peak accounts for about 10.2% of the total bead population. In the case of one cell per droplet, it was expected to have about 63.2% of the beads in the brighter mode, while the FACS analysis result indicated that about 51.0% of the beads were highly fluorescent. The relative deviation was less than 20%, which might be due to error in cell counting, or the nonuniformity of droplet and bead concentrations. The mean DNA amount on the beads in the brighter peak was about 150 attomoles. The results show that the material amplified from a single cell in a single droplet on a single bead is enough for FACS analysis.

The methods and devices described herein may also be used to detect multiple targets from different strains, e.g., different *E. coli* strains. For example, different stains of *E. coli* (e.g., a laboratory strain K12, an "atypical" enteropathogenic *E. coli* EPEC strain O55:H7, and an enterohemorrhagic, shigatoxin producing *E. coli* (EHEC/STEC) strain O157:H7) may be detected. For analysis of three targets, in addition to a primer set targeting species-specific 16R rRNA primers, three sets of primers are used in the multiplex analysis, e.g., a primer set targeting yai X gene specific to *E. coli* K12, a primer set specific for a portion of the bfpA gene encoding the *E. coli* O55:H7 bundle-forming pilus, and a primer set specific for the shigatoxin I (stxI) gene present in enterohemorrhagic strains of *E. coli* such as O157:H7.

In the single target analysis, only one detection wavelength may be used in the FACS. Multiplex analysis requires an instrument capable of analyzing multiple colors at the same time, e.g., a Beckman-Coulter EPICS XL-MCL analyzer, a Beckman-Coulter FC-500 analyzer and advanced cell sorters. The XL-MCL analyzer has a 488 nm argon laser, which allows four-color analysis. The FC-500 has a 488 nm argon laser and a 633 nm HeNe laser and can simultaneously measure up to 5 color parameters. At least three different strains of cells can be studied at the same time with 2 genomic markers for each cell, e.g., one for species-specific 16S RNA and another specific for the strain.

Each bead is labeled with an equal amount of reverse primer for each gene of interest. For example, forward primer for R16 rRNA, yaiX, bfpA, sltI, will be labeled with Fluorescein (green), Tetramethylrhodamine (Orange-red), Texas Red (red), and Cy5 (far-red), respectively. The cells are introduced into droplets in the same way discussed above. Multiple-gene analysis is then performed with the different types of cells under consideration. With the same concentration of each type of cell in the cell sample, it is expected that the same number of representative beads in the FACS result will be observed. In addition to testing different types of cells, multiple-marker analysis can be performed from a single strain to detect multiple genes from a single cell.

In certain embodiments, the single cell assay is used to detect low levels of pathogenic variants in the presence of high commensal backgrounds. For example, as *E. coli* is a commensalbacteria, the ability to detect pathogenic species from a large population of nonpathogenic *E. coli* is of significant interest to the area of pathogen detection. In addition to the detection of *E. coli*, detection of other pathogenic bacteria such as MSSA and MRSA *Staph. aureus* may be performed.

Because each agarose bead will be conjugated with multiple reverse primers, the maximum amount of amplicon for any specific gene will drop significantly when the number of targets to be studied increases. At least 150 attomoles of amplicon can be produced on a single bead. Potentially, one bead could be used to study dozens of genes at the same time as the detection limit of most flow cytometers extends down to 1000 fluorescent labels. Adding more targets would require the use of combinatorial and/or Energy-Transfer labels to expand the number of fluorescent codes.

Detection and Genetic Analysis of Transformed Cancer Cells

The μDG 600 also enables high-throughput single cell PCR to detect and genotype cells with mutations at low <1/1000 cell frequency levels or below. For example, serially diluted leukemia or lymphoma cell lines harboring mutations, such as translocation t(14;18) and mutations in NRAS and NPM1, can be detected in a background of normal cells.

In an example, single cell genetic analysis (SCGA) of t(14;18)(IgH/BCL2) in the RL lymphoma cell line may be performed. The following primers and probes, with an underlined modification to the probe, are currently used to detect t(14;18):

```
Forward    RT0001     5'-TGG CGAATGACCAGCAGATT-3'
Primer

Reverse    JH EXO     5'-ACT CAC CTG AGG AGA CGG
Primer

TGAC-3'    BCL-2      5'-FAM-TTT CAA CAC AGA CCC ACC
Probe      MBR TM2    CAG AGC CCT CCT G-3'-TAMRA
```

DNA quality may be confirmed by qPCR of the β-actin gene using 100 ng of DNA and genomic DNA analyzed for t(14;18) using the following conditions: 1× Taq Gold buffer, 5 mM $MgCl_2$, 400 μM dUTP, 200 μM each of dATP, dCTP, dGTP, 200 μM of each primer and probe, 0.5 U of AmpEraseuracil N-glycosylase, and 1.25 U of AmpliTaq Gold (Applied Biosystems) in 50 μl. PCR conditions include an incubation at 50° C. for 2 min, followed by 50 cycles of 15 s at 95° C., 30 s at 55° C., and 30 s at 72° C. The t(14;18) sequence from the RL cell line (ATCC CRL-2261) cloned into the pCR® 2.1 plasmid (Invitrogen, Carlsbad, Calif.) can be used as the standard, diluted into human lymphoblastoid TK6 cell line at $3-3\times10^5$ copies. The assay routinely detects 3 copies of template in 1 μg of background DNA in 2 out of 3 replicates and standard curves consistently yield $R^2$ values greater than 0.99. Nested PCR and DNA sequencing for t(14;18) can be carried out as described previously to confirm preparations.

The below examples refer to leukemia and lymphoma cell lines shown in Table 1.

TABLE 1

Leukemia and Lymphoma Cell Lines

| Mutation | Cell line | Resource | Reference |
|---|---|---|---|
| t(14; 18) | RL | ATCC | Beckwith M, et al. Phorbol ester-induced, cell-cycle-specific, growth inhibition of human B-lymphoma cell lines. J. Natl. Cancer Inst. 1990, 82: 501-509. |
| NPM1 | OCI/AML3 | DSMZ | Quentmeier H, et al. Cell line OCI/AML3 bears exon-12 NPM gene mutation-A and cytoplasmic expression of nucleophosmin. Leukemia. 2005, 19: 1760-1767. |
| N-RAS | KG-1 | ATCC | Sheng XM, et al. Mutations of the RAS genes in childhood acute myeloid leukemia, myelodysplastic syndrome and juvenile chronic myelocytic leukemia. Leuk Res. 1997, 21: 697-701. |

Using the t(14;18) sequence from RL cells (CRL-2261 from ATCC) cloned into the pCR 2.1 plasmid, a bead-based PCR amplification system is developed. Having established a bead-based PCR amplification system in a traditional bulk emulsion process, the methods involve introducing the t(14; 18) plasmid into the uniform nL droplets and performing PCR with beads. In certain embodiments, intact RL lymphoma cells are introduced into the droplets and SCGA is performed. To establish how sensitive the assay is, RL lymphoma cells may be serially diluted in a background of human TK6 lymphoblastoid cells which lack t(14;18). After PCR, the free strand will be denatured and removed from the beads, and then the beads will be incubated with different fluorescently labeled probes specific for the mutant and wild type product. In certain embodiments, the methods can be used to analyze more than 1 million beads in 15 minutes by flow cytometry so a 1 in a million mutation frequency is feasible. In certain embodiments under time constraints, a smaller mutation frequency (e.g., 1 in 10,000 mutation frequency) may be imposed. For example, using a single array μDG, a mutation frequency of 1 in 100,000 can be analyzed in ~3.5 hrs while a 1 in a million mutation frequency will require 35 hrs of droplet generation.)

In another example, SCGA analysis of mutations in NRAS (at codon 12) and NPM1 (in Exon 12) may be performed. A similar approach will be taken to establish SCGA methods for the analysis of NRAS mutations at codon 12 and NPM1 mutations in Exon 12. An allele-specific amplification method (ARMS), a highly sensitive one-stage allele-specific PCR, may be used for amplification of NRAS and KRAS mutations. This method employs a mutant-specific sense primer, with a double mismatch at the 3' end created by introducing a mutation on the penultimate base to enhance specificity and reduce false positive results. Specifically the sense primer N1221 5'-CTGGTGGTGGTTGGAGCAAA-3' along with the reverse primer 1206L is used to detect the GGT(Gly)-GAT(Asp) alteration in the KG-1 cell line. The PCR reaction mixture contains 10 mMTris HCL, 1.5 mM $MgCl_2$, 0.01% (w/v) gelatin, 50 mM KCL, 200 mM of each dNTP, 50 pmol of each primer, 1.25 U of AmpliTaq Gold, and 100 ng of DNA. Amplification conditions are 10 min at 94° C. followed by 38 cycles of 30 s at 94° C., 1.5 min at 67° C., and 1.5 min at 70° C. As usual for SCGA, the free primer is fluorescently labeled. PCR products are sequenced for confirmation as described.

In certain embodiments, the methods involve serially diluting the KG-1 cells in a background of human cells with wild-type NRAS sequence to establish how sensitive the assay can be made. According to various embodiments, the assay may be used to detect mutations at mutation frequencies as low as 1 in 10,000 to 1 in 1 million (depending on time considerations). In another embodiment, the assay is adapted to detect all NRAS mutations (codons 12, 13 and 61) in a multiplex assay.

In another example, a NPMl assay targeting the most common mutation (mutation A), a duplication of a TCTG tetranucleotide at positions 956 through 959 of the reference sequence (GenBank accession number NM_002520) is performed. The sense primer gNPMmut A-F 5'-AGGCTATTCAAGATCTCTGTCTGG-3' and the reverse primer gNPM-R2 5'-AGTTCTCACTCTGCATTATAAAAGGA-3' can be used to amplify NPM1 mutation A from the OCI/AML3 cell line with the signal detected by a fluorescent oligonucleotide probe designed to selectively bind the mutant DNA only. PCR reactions (25 μL) contain 2.5μ TaqMan buffer A, 5 mM $MgCl_2$, 0.3 mM each dATP, dCTP and dGTP, 0.6 mMdUTP, 5 μM primers, 1.25 U AmpliTaq Gold and 500 ng DNA. The amplification protocols is 10 min at 95° C., followed by target amplification via 50 cycles of 15 s at 95° C. and 1 min at 61° C. After PCR, the free strand is denatured and removed from the beads so that only the bound strand remains. Then the beads are incubated with fluorescently labeled probes specific for the mutant and wild-type targets. Beads containing the mutation are detected using FACS. The expected sensitivity is 1/1000 when mutant cells are diluted in normal wild type cells. NPM1 mutations A through H may also be detected using specific forward primers in a multiplex assay.

In an example of multiplex SCGA analysis, the multiplexing of all 3 assays so that t(14;18) and mutations in NRAS and NPM1 are detected in single cells in a mixed population of cells by SCGA analysis is performed. For example, the cell lines listed in the Table 1 above are mixed and a multiplex assay detects the relative proportions of the mutant cells in the mixture. In this example, and with other assays that may be performed using the μDG, the optimal primer annealing temperatures may be variable and may require standardization of the assays at a specific temperature. Performing these amplifications in separate nL volumes (as is possible only with the μDG methods) reduces problems of nonspecific/false amplification because false hybridization of a primer in one bolus does not effect reactions in the other bolus. Furthermore the products of the PCR will be much more concentrated thereby improving PCR efficiency even when the annealing temperature is not exactly at the optimum.

While the invention has been particularly shown and described with reference to specific embodiments, it will also be understood by those skilled in the art that changes in the form and details of the disclosed embodiments may be made without departing from the spirit or scope of the invention. For example, the embodiments described above may be implemented using a variety of materials. Therefore, the scope of the invention should be determined with reference to the appended claims.

What is claimed is:

1. A microdroplet generator comprising:
   a nozzle;
   a reagent inlet to a reagent channel;
   a plurality of oil inlets to a plurality of oil channels;
   a pneumatic layer comprising a plurality of pneumatic channels;
   a first fluidic layer comprising the reagent channel;
   an elastomeric layer sandwiched between the pneumatic layer and the first fluidic layer;
   a three-valve pump comprising valve displacements in the plurality of pneumatic channels aligned with discontinuities in the reagent channel and configured to provide monodisperse pulsatile flow of reagent from the reagent inlet to the nozzle via the reagent channel, the nozzle comprising a junction of the reagent channel and the oil channels and configured to form monodisperse emulsion droplets; and
   a droplet outlet.

2. The microdroplet generator of claim 1 further comprising a second fluidic layer, said second fluidic layer comprising the nozzle.

3. The microdroplet generator of claim 2 further comprising a via connecting the reagent channel to the second fluidic layer.

4. The microdroplet generator of claim 1 wherein the first fluidic layer further comprises the nozzle and the oil channels.

5. The microdroplet generator of claim 1 wherein the three-valve pump is configured to provide monodisperse pulses having volumes ranging from 100 pL to 10 nL.

6. The microdroplet generator of claim 1 wherein the reagent channel is a hybrid glass-elastomer channel.

7. The microdroplet generator of claim 1 wherein the generator is configured to form monodisperse emulsion droplets at a frequency of 0.01-100 Hz.

8. A microdroplet generator comprising
   a reagent inlet connected to a plurality of glass-elastomeric hybrid reagent channels;
   a plurality of three-valve elastomeric valves configured to produce pulsatile flow of reagent mix in the plurality of glass-elastomeric hybrid channels and pump the reagent mix to a plurality of nozzles;
   a pneumatic layer comprising a plurality of pneumatic lines configured to simultaneously control the three-valve pumps;
   a plurality of injectors;
   a plurality of outlets; and
   a plurality of oil channels connected to the plurality of injectors, the plurality of injectors configured to produce monodisperse emulsion droplets and flow said emulsion droplets to the plurality of outputs.

9. A method of generating microdroplets, the method comprising:
   providing a reagent and target mixture to a reagent inlet channel on a microfabricated structure;
   forming droplets of the mixture in the channel via an in-channel three-valve elastomeric pump, wherein a pumping frequency of the three-valve elastomeric pump and a droplet formation frequency have a 1:1 correspondence; and
   routing the droplets to an injector to form monodisperse emulsion droplets encapsulating the reagent and target mixture, wherein no more than a single target is encapsulated in the majority of emulsion droplets.

10. The method of claim 9 wherein the volume of the droplets is between about 100 pL-100 nL.

11. The method of claim 9 wherein the volume of the droplets is between 2 and 5 nL.

12. The method of claim 9 wherein the reagent and target mixture further comprises a microcarrier element.

13. The method of claim 9 wherein the reagent and target mixture comprises PCR reagent, primer functionalized microcarrier elements, and target.

14. The method of claim 13 wherein forming monodisperse emulsion droplets comprises forming emulsion droplets encapsulating PCR reagent, a single primer functionalized microcarrier element and a single target.

15. The method of claim 9 wherein the target is a cell or molecule.

16. A microdroplet generator comprising:
   a reagent inlet to a reagent channel;
   an injector;
   a plurality of oil inlets to a plurality of oil channels;
   a pneumatic layer comprising a plurality of pneumatic channels;
   a first fluidic layer comprising the reagent channel;
   an elastomeric layer sandwiched between the pneumatic layer and the first fluidic layer;
   a micro-pump comprising valve displacements in the plurality of pneumatic channels aligned with discontinuities in the reagent channel and configured to provide pulsatile flow of reagent from the reagent inlet to the injector via the reagent channel, the injector configured to form emulsion droplets; and
   a droplet outlet.

17. The microdroplet generator of claim 16 wherein the generator is configured to form monodisperse emulsion droplets at a frequency of 0.01-100 Hz.

18. The microdroplet generator of claim 16 wherein the generator is configured to form monodisperse emulsion droplets at a frequency of 1-50 Hz.

19. The microdroplet generator of claim 16 wherein the generator is configured to form monodisperse emulsion droplets at a frequency of 1-10 Hz.

* * * * *

UNITED STATES PATENT AND TRADEMARK OFFICE
CERTIFICATE OF CORRECTION

PATENT NO. : 8,454,906 B2  
APPLICATION NO. : 12/670377  
DATED : June 4, 2013  
INVENTOR(S) : Mathies et al.

Page 1 of 1

It is certified that error appears in the above-identified patent and that said Letters Patent is hereby corrected as shown below:

On the Title Page,

At section (75) Inventors:

Change inventor's name from "Chaoyang Yang" to --Chaoyong Yang--.

Signed and Sealed this  
Fifteenth Day of October, 2013

Teresa Stanek Rea  
*Deputy Director of the United States Patent and Trademark Office*